(12) United States Patent
Irisawa

(10) Patent No.: US 11,304,607 B2
(45) Date of Patent: Apr. 19, 2022

(54) PHOTOACOUSTIC IMAGE GENERATION APPARATUS, SIGNAL PROCESSING DEVICE, AND PHOTOACOUSTIC IMAGE GENERATION METHOD

(71) Applicant: FUJIFILM Corporation, Tokyo (JP)

(72) Inventor: Kaku Irisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1195 days.

(21) Appl. No.: 15/358,863

(22) Filed: Nov. 22, 2016

(65) Prior Publication Data

US 2017/0071475 A1   Mar. 16, 2017

Related U.S. Application Data

(63) Continuation of application No. PCT/JP2015/056792, filed on Mar. 9, 2015.

(30) Foreign Application Priority Data

Jun. 30, 2014 (JP) .............................. JP2014-134044

(51) Int. Cl.
  *A61B 5/00* (2006.01)
  *A61B 1/00* (2006.01)
  (Continued)

(52) U.S. Cl.
  CPC ........ *A61B 5/0095* (2013.01); *A61B 1/00006* (2013.01); *A61B 1/07* (2013.01);
  (Continued)

(58) Field of Classification Search
  CPC ..... A61B 5/0095; A61B 1/00006; A61B 1/07; A61B 8/4416; A61B 8/08; A61B 17/3403;
  (Continued)

(56) References Cited

U.S. PATENT DOCUMENTS 4,484,820 A * 11/1984 Rosencwaig ...... G01N 21/1702
                                                        374/6
5,070,733 A * 12/1991 Nagata ............... G01N 29/0609
                                                       73/602
(Continued)

FOREIGN PATENT DOCUMENTS

JP   2009-31262 A    2/2009
JP   2010-512929 A   4/2010
(Continued)

OTHER PUBLICATIONS

International Search Report for PCT/JP2015/056792 (PCT/ISA/210) dated Apr. 7, 2015.
(Continued)

*Primary Examiner* — Amanda Lauritzen Moher
*Assistant Examiner* — Amy J Shafqat
(74) *Attorney, Agent, or Firm* — Birch, Stewart, Kolasch & Birch, LLP

(57) ABSTRACT

An insertion needle 15 has a photoacoustic wave generating portion that generates a photoacoustic wave by absorbing light emitted from a laser unit 13. A photoacoustic image generation unit 25 generates a photoacoustic image based on the detection signal of the photoacoustic wave emitted from the insertion needle 15. The sound source position detection unit 30 detects the photoacoustic wave generating source from the photoacoustic image. A first signal acquisition unit 31 acquires an S value, and a second signal acquisition unit 32 acquires an N value. A light emission control unit 33 controls the number of light emissions and the light emission interval of the laser unit 13 for one photoacoustic image generation based on the ratio between the S value and the N value. The photoacoustic image generation unit 25 generates a photoacoustic image by at least adding the detection
(Continued)

signals of photoacoustic waves corresponding to the number of light emissions.

18 Claims, 9 Drawing Sheets

(51) Int. Cl.
*A61B 1/07* (2006.01)
*A61B 17/34* (2006.01)
*A61B 8/08* (2006.01)
*A61B 8/00* (2006.01)
*A61B 5/06* (2006.01)
*A61B 8/12* (2006.01)

(52) U.S. Cl.
CPC ............. *A61B 5/061* (2013.01); *A61B 5/6848* (2013.01); *A61B 8/08* (2013.01); *A61B 8/12* (2013.01); *A61B 8/4416* (2013.01); *A61B 17/3403* (2013.01); *A61B 2017/3413* (2013.01); *A61B 2576/00* (2013.01)

(58) Field of Classification Search
CPC ........ A61B 2576/00; A61B 2017/3413; A61B 8/12; A61B 8/5215; A61B 8/5223; A61B 5/7225; G01N 29/30; G01N 29/2418; G01N 29/2425; G16H 50/20; G01S 15/8965; G01S 15/8968; G01S 15/8906
See application file for complete search history.

(56) References Cited

U.S. PATENT DOCUMENTS

| | | | | |
|---|---|---|---|---|
| 5,491,329 | A * | 2/1996 | Urakami | A61B 5/0059 250/205 |
| 8,249,405 | B2 * | 8/2012 | Ishii | H01S 5/1032 385/32 |
| 9,116,111 | B2 * | 8/2015 | Nakajima | G01N 21/1702 |
| 2006/0018539 | A1 * | 1/2006 | Sato | G06K 9/36 382/173 |
| 2009/0187099 | A1 * | 7/2009 | Burcher | A61B 5/0095 600/430 |
| 2009/0310885 | A1 * | 12/2009 | Tamaru | H04N 5/23212 382/275 |
| 2010/0037695 | A1 * | 2/2010 | Tsujita | G01N 21/1702 73/587 |
| 2010/0049044 | A1 | 2/2010 | Burcher | |
| 2010/0174197 | A1 | 7/2010 | Nakajima et al. | |
| 2010/0249570 | A1 * | 9/2010 | Carson | A61B 5/0059 600/407 |
| 2012/0183190 | A1 * | 7/2012 | Fukutani | A61B 5/0073 382/128 |
| 2013/0245418 | A1 * | 9/2013 | Oishi | A61B 5/0095 600/407 |
| 2014/0233686 | A1 * | 8/2014 | Choi | G01N 29/4463 375/349 |
| 2014/0275941 | A1 * | 9/2014 | Kang | A61B 5/7203 600/407 |
| 2014/0341244 | A1 * | 11/2014 | Minneman | H01S 5/0654 372/38.02 |
| 2015/0297092 | A1 * | 10/2015 | Irisawa | A61B 5/0095 600/407 |
| 2015/0351639 | A1 * | 12/2015 | Abe | A61B 8/4416 600/407 |
| 2016/0022149 | A1 * | 1/2016 | Asao | A61B 5/0095 600/407 |
| 2016/0135689 | A1 * | 5/2016 | Murakoshi | A61B 5/6848 600/407 |
| 2016/0310109 | A1 * | 10/2016 | Park | A61B 8/5207 |
| 2017/0112474 | A1 * | 4/2017 | Burcher | A61B 8/14 |
| 2017/0188839 | A1 * | 7/2017 | Tashiro | A61B 1/00 |

FOREIGN PATENT DOCUMENTS

| | | |
|---|---|---|
| JP | 2011-229815 A | 11/2011 |
| JP | 2013-13713 A | 1/2013 |
| JP | 2013-27513 A | 2/2013 |
| JP | 2013-192857 A | 9/2013 |

OTHER PUBLICATIONS

Written Opinion of the International Searching Authority for PCT/JP2015/056792 (PCT/ISA/237) dated Apr. 7, 2015.
International Preliminary Report on Patentability and the English translation of the Written Opinion of the International Searching Authority (Forms PCT/IB/326, PCT/IB/373 and PCT/ISA/237), dated Jan. 12, 2017, for International Application No. PCT/JP2015/056792.

* cited by examiner

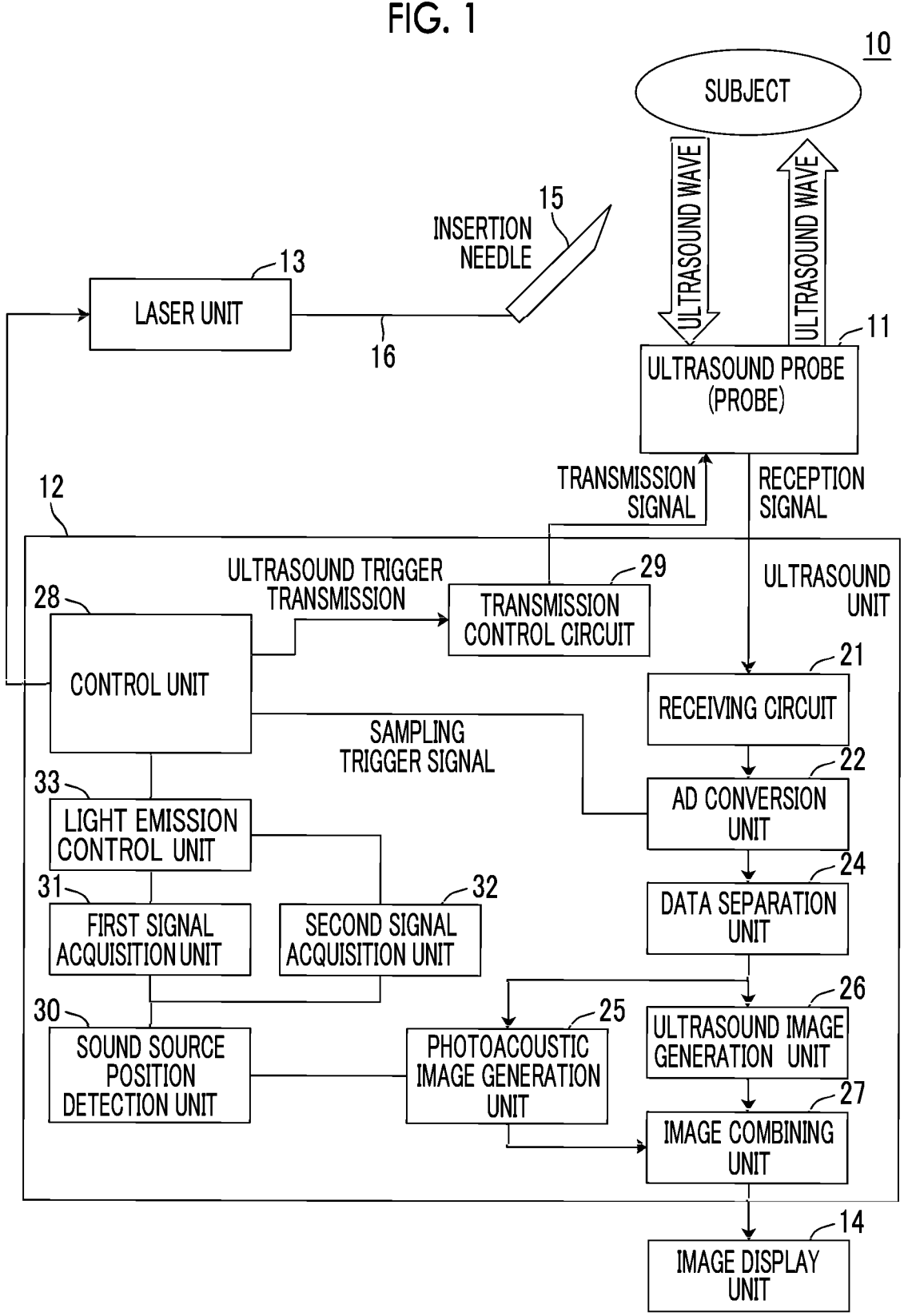

| SN MAGNIFICATION | NUMBER OF LIGHT EMISSIONS | SUM OF LIGHT EMISSIONS | FIRST LINE POSITION | LINE INTERVAL |
|---|---|---|---|---|
| 1 | 1 | 2 | 32 | 64 |
| 2 | 4 | 8 | 8 | 16 |
| 4 | 16 | 32 | 2 | 4 |
| 8 | 64 | 128 | 0.5 | 1.0 |

PHOTOACOUSTIC IMAGE GENERATION APPARATUS, SIGNAL PROCESSING DEVICE, AND PHOTOACOUSTIC IMAGE GENERATION METHOD

CROSS-REFERENCE TO RELATED APPLICATIONS

This application is a Continuation of PCT International Application No. PCT/JP2015/056792 filed on Mar. 9, 2015, which claims priority under 35 U.S.C. § 119 (a) to Japanese Patent Application No. 2014-134044 filed on Jun. 30, 2014. Each of the above application(s) is hereby expressly incorporated by reference, in its entirety, into the present application.

BACKGROUND OF THE INVENTION

1. Field of the Invention

The present invention relates to a photoacoustic image generation apparatus, a signal processing device, and a photoacoustic image generation method, more specifically, to a photoacoustic image generation apparatus, a signal processing device, and a photoacoustic image generation method for generating a photoacoustic image by detecting photoacoustic waves generated in a subject after emitting light to the subject.

2. Description of the Related Art

As a kind of image examination method capable of examining the state of the inside of the body in a non-invasive manner, ultrasonography is known. In ultrasound examination, an ultrasound probe capable of transmitting and receiving ultrasound waves is used. When ultrasound waves are transmitted to a subject (body) from the ultrasound probe, the ultrasound waves propagate through the body to be reflected on the tissue interface. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of the body using the photoacoustic effect is known. In general, in photoacoustic imaging, pulsed laser light, such as a laser pulse, is emitted into the body. In the body, living tissue absorbs the energy of the pulsed laser light, and ultrasound waves (photoacoustic waves) due to adiabatic expansion due to the energy are generated. By detecting the photoacoustic waves using an ultrasound probe or the like and forming a photoacoustic image based on the detection signal, it is possible to visualize the inside of the body based on the photoacoustic waves.

For photoacoustic imaging, JP2009-31262A discloses a combination of photoacoustic imaging and treatment using an insertion needle. In JP2009-31262A, an affected part such as a tumor, a part suspected to be an affected part, or the like is found by generating a photoacoustic image and observing the image. In order to examine such a part more precisely or in order to perform injection into the affected part, sampling of cells, injection into the affected part, and the like are performed using an insertion needle, such as an injection needle or a cytodiagnosis needle. In JP2009-31262A, it is possible to perform insertion while observing the affected part using a photoacoustic image.

In addition, JP2013-13713A also discloses a combination of photoacoustic imaging and an insertion needle. In JP2013-13713A, the insertion needle has a light emitting portion. Light emitted from a laser light source is guided to the light emitting portion of the insertion needle using, for example, an optical fiber, and is emitted to the outside from the light emitting portion. By detecting photoacoustic waves, which are generated by absorbing the light emitted from the light emitting portion of the insertion needle, using an ultrasound probe and generating a photoacoustic image based on the detection signal, it is possible to check the position of the insertion needle.

SUMMARY OF THE INVENTION

In the case of generating photoacoustic waves in the insertion needle, when the insertion needle is inserted to a deep position, it is not possible to detect the photoacoustic waves with sufficient intensity by the ultrasound probe placed on the body surface. Accordingly, there is a case where the Signal to Noise Ratio (SN ratio) of the generated photoacoustic image is reduced. As a method for improving the SN ratio, averaging a plurality of pieces of measurement data is known. In general, it is possible to increase the SN ratio by increasing the number of times of averaging.

The averaging of photoacoustic waves is disclosed in JP2011-229815A, for example. In JP2011-229815A, the number of times of averaging is determined such that the SN ratio after averaging is equal to or greater than a value set in advance. In JP2011-229815A, however, since the number of times of averaging is increased only when the SN ratio is low, a period for detection of photoacoustic waves remains constant. Accordingly, as the number of times of averaging is increased in order to improve the SN ratio, the number of photoacoustic images generated per unit time is reduced by the increased amount.

The above problem is not limited to the insertion needle, and can also occur in the case of trying to check the positions of other inserts inserted into the subject, such as a catheter or a guide wire, using photoacoustic waves generated in these inserts.

In view of the above, it is an object of the present invention to provide a photoacoustic image generation apparatus, a signal processing device, and a photoacoustic image generation method capable of improving the image quality of a photoacoustic image without reducing the number of photoacoustic images generated per unit time when it is possible to check the position of an insert using a photoacoustic image.

In order to achieve the aforementioned object, the present invention provides a photoacoustic image generation apparatus comprising: a light source; an insert at least a part of which is inserted into a subject and which has a light guide member for guiding light emitted from the light source, a light emitting portion that emits light guided by the light guide member, and a photoacoustic wave generating portion that generates a photoacoustic wave due to the light emitted from the light emitting portion; an acoustic wave detection unit that detects a photoacoustic wave emitted from the insert after at least a part of the insert is inserted into the subject; a photoacoustic image generation unit that generates a photoacoustic image based on a detection signal of the photoacoustic wave; a sound source position detection unit that detects a position of a generation source of the photoacoustic wave from the photoacoustic image; a first signal acquisition unit that acquires a first signal value indicating an intensity of the photoacoustic wave emitted from the generation source of the photoacoustic wave; a second signal acquisition unit that acquires a signal value, which indicates noise in the photoacoustic image, as a second signal value; and a light emission control unit that controls the number of light emissions and a light emission interval of the light source for one photoacoustic image generation based on a ratio between the first signal value and the second signal value. The photoacoustic image generation unit generates a photoacoustic image by at least adding detection signals of photoacoustic waves corresponding to the number of light emissions.

In the present invention, it is preferable that the light emission control unit makes the number of light emissions of the light source larger than the current number of light emissions and makes the light emission interval shorter than a current light emission interval when a value obtained by dividing the first signal value by the second signal value is smaller than a first threshold value.

It is preferable that the light emission control unit makes the number of light emissions of the light source smaller than the current number of light emissions and makes the light emission interval longer than the current light emission interval when the value obtained by dividing the first signal value by the second signal value is larger than a second threshold value that is larger than the first threshold value.

The light emission control unit may make the light source emit light at equal intervals until generation of a next photoacoustic image after generation of one photoacoustic image.

The sound source position detection unit may detect a position of a pixel having a maximum pixel value in the photoacoustic image as the position of the generation source of the photoacoustic wave.

The first signal acquisition unit may acquire, as the first signal value, a pixel value of a pixel of a photoacoustic image at the position of the generation source of the photoacoustic wave or a signal value of a detection signal of the photoacoustic wave.

Alternatively, the first signal acquisition unit may acquire, as the first signal value, a value obtained by subtracting an average value of pixel values of the photoacoustic image corresponding to a plurality of positions around the position of the generation source of the photoacoustic wave or an average value of signal values of detection signals of the photoacoustic waves from a pixel value of a pixel of a photoacoustic image at the position of the generation source of the photoacoustic wave or a signal value of a detection signal of the photoacoustic wave.

The second signal acquisition unit may calculate a variance of pixel values of the photoacoustic image corresponding to a plurality of positions around the position of the generation source of the photoacoustic wave or a variance of signal values of detection signals of the photoacoustic waves, and acquire the calculated variance as the second signal value.

The acoustic wave detection unit may further detect a reflected acoustic wave of an acoustic wave transmitted toward the subject, and the photoacoustic image generation apparatus may further have a reflected acoustic wave image generation unit that generates a reflected acoustic wave image based on the reflected acoustic wave.

The photoacoustic image generation unit and the reflected acoustic wave image generation unit may repeatedly generate the photoacoustic image and the reflected acoustic wave image, respectively. In this case, the number of photoacoustic images generated per unit time and the number of reflected acoustic wave images generated per unit time may be the same.

The acoustic wave detection unit may include at least a plurality of detector elements arranged in a one-dimensional manner, and may detect the reflected acoustic wave by performing a scan while shifting an acoustic line by one line at a time.

In the above, the light emission control unit may make the light source emit light between scans of the acoustic lines.

The light emission control unit may control emission of the light source with reference to a look-up table in which the number of light emissions is associated with an emission timing for determining between which scanning positions in detection of a reflected ultrasound wave each emission is to be performed.

A configuration further including an image combining unit that combines the photoacoustic image and the reflected acoustic wave image is also a preferred aspect of the present invention.

It is preferable that the photoacoustic image generation apparatus of the present invention further has a noise reduction processing unit that performs noise reduction filtering processing for reducing noise of the photoacoustic image and that the sound source position detection unit detects the position of the generation source of the photoacoustic wave from a photoacoustic image after performing the noise reduction filtering processing.

The noise reduction filtering processing may include, for example, median filtering processing or Gaussian filtering processing.

In addition, the noise reduction filtering processing may include filtering processing for reducing noise incorporated to positions in the same depth direction in detection signals of a plurality of elements. The filtering processing may include processing for adding the detection signals of a plurality of detector elements to be simultaneously detected or performing averaging after adding the detection signals at each depth position and subtracting a signal obtained by the addition or a signal obtained by the averaging from the detection signal detected by each detector element.

It is preferable that the photoacoustic image generation apparatus of the present invention further has an image display unit that displays the photoacoustic image, a maximum value of the first signal value, and a current first signal value on a screen.

In addition, the present invention provides a signal processing device comprising: a receiving circuit that receives a detection signal of a photoacoustic wave emitted from an insert at least a part of which is inserted into a subject and which has a light guide member for guiding light emitted from a light source, a light emitting portion that emits light guided by the light guide member, and a photoacoustic wave generating portion that generates a photoacoustic wave due to the light emitted from the light emitting portion; a photoacoustic image generation unit that generates a photoacoustic image based on a detection signal of the photoacoustic wave; a sound source position detection unit that detects a position of a generation source of the photoacoustic wave from the photoacoustic image; a first signal acquisition unit that acquires a first signal value indicating an intensity of the photoacoustic wave emitted from the generation source of the photoacoustic wave; a second signal acquisition unit that acquires a signal value, which indicates noise in the photoacoustic image, as a second signal value; and a light emission control unit that controls the number of light emissions and a light emission interval of the light source for one photoacoustic image generation based on a relative magnitude relationship between the first signal value and the second signal value. The photoacoustic image generation unit generates a photoacoustic image by at least adding detection signals of photoacoustic waves corresponding to the number of light emissions.

In addition, the present invention provides a photoacoustic image generation method including: a step of receiving a detection signal of a photoacoustic wave emitted from an insert having a light guide member for guiding light emitted from a light source, a light emitting portion that emits light guided by the light guide member, and a photoacoustic wave generating portion that generates a photoacoustic wave due to the light emitted from the light emitting portion; a step of generating a photoacoustic image based on a detection signal of the photoacoustic wave; a step of detecting a position of a generation source of the photoacoustic wave from the photoacoustic image; a step of acquiring a first signal value indicating an intensity of the photoacoustic wave emitted from the generation source of the photoacoustic wave; a step of acquiring a signal value, which indicates noise in the photoacoustic image, as a second signal value; and a step of determining the number of light emissions and a light emission interval of the light source for one photoacoustic image generation based on a relative magnitude relationship between the first signal value and the second signal value. In the step of generating the photoacoustic image, a photoacoustic image is generated by at least adding detection signals of photoacoustic waves corresponding to the number of light emissions.

In the photoacoustic image generation apparatus, the signal processing device, and the photoacoustic image generation method of the present invention, when it is possible to check the position of an insert using a photoacoustic image, it is possible to improve the image quality of a photoacoustic image without reducing the number of photoacoustic images generated per unit time.

BRIEF DESCRIPTION OF THE DRAWINGS

FIG. 1 is a block diagram showing a photoacoustic image generation apparatus according to an embodiment of the present invention.

DESCRIPTION OF THE PREFERRED EMBODIMENTS

Figure 2A:
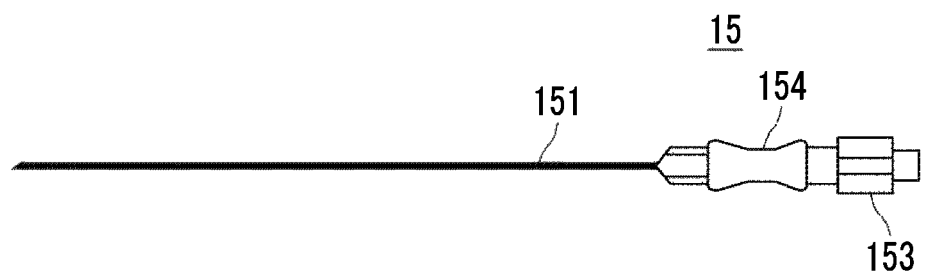
FIG. 2A shows the appearance of the entire insertion needle.

Hereinafter, embodiments of the present invention will be described in detail with reference to the diagrams. FIG. 1 shows a photoacoustic image generation apparatus according to an embodiment of the present invention. A photoacoustic image generation apparatus 10 includes a probe (ultrasound probe) 11, an ultrasound unit 12, a laser unit 13, and an insertion needle 15. In the embodiment of the present invention, an ultrasound wave is used as a photoacoustic wave. However, the present invention is not limited to the ultrasound wave, and an acoustic wave having an audible frequency may be used as long as an appropriate frequency can be selected according to an examination target, measurement conditions, or the like.

The laser unit 13 that is a light source is configured as a laser diode light source (semiconductor laser light source), for example. Types of light sources are not particularly limited, and the laser unit 13 may be an optical amplification type laser light source using a laser diode light source as a seed light source. Alternatively, a solid state laser light source using an yttrium aluminum garnet (YAG), alexandrite, or the like may be used. Laser light emitted from the laser unit 13 is guided to the insertion needle 15, for example, using a light guide unit, such as an optical fiber 16. Light sources other than the laser light source may be used.

Figure 2B:
FIG. 2B shows the appearance of the insertion needle body.
Figure 2C:
FIG. 2C shows the appearance of an inner needle.

FIG. 2A shows the appearance of the entire insertion needle, FIG. 2B shows the appearance of the insertion needle body, and FIG. 2C shows the appearance of an inner needle. The insertion needle 15 has an insertion needle body 151, which forms an outer needle, and an inner needle 152. The insertion needle body 151 is bonded to an outer needle base 154 (refer to FIG. 2B), and the inner needle 152 is bonded to an inner needle base 153 (refer to FIG. 2C). The optical fiber 16 that connects the laser unit 13 (refer to FIG. 1) and the insertion needle 15 to each other has an optical connector at its distal end (far-end side when viewed from the laser unit 13). An optical connector for connection with the optical connector of the optical fiber 16 is provided in the inner needle base 153 of the insertion needle 15.

The insertion needle body 151 has an opening at the distal end formed at an acute angle, and has an inner cavity therein. The inner needle 152 has an outer diameter of approximately the same size as the inner cavity of the insertion needle body 151 forming the outer needle, and is configured so as to be able to be inserted into or removed from the hollow insertion needle body 151. The inner needle 152 is inserted into the inner cavity of the insertion needle body 151 from the outer needle base 154 side, thereby sealing at least a part of the inner cavity of the insertion needle body 151 to the extent that a cut piece of the body or the like is prevented from entering the inner cavity. A protruding portion for connection alignment is provided in the inner needle base 153, and a groove engaged with the protruding portion of the inner needle base 153 is provided in the outer needle base 154. When setting the inner needle 152 into the insertion needle body 151, the inner needle base 153 is fitted to the outer needle base 154 after aligning the position of the protruding portion of the inner needle base 153 and the position of the groove of the outer needle base 154.

An operator inserts the insertion needle 15 into a subject in a state where the inner needle 152 is set into the insertion needle body 151 (refer to FIG. 2A). Since the inner cavity of the insertion needle body 151 is clogged with the inner needle 152, it is possible to prevent a piece of flesh or the like from entering the inner cavity while the needle is being inserted. Accordingly, it is possible to prevent the insertion feeling of the operator from being adversely affected. In addition, it is possible to prevent the inflow of water from the insertion part to the inner cavity of the insertion needle body 151. After the insertion into the subject, the operator releases the connection between the inner needle base 153 and the outer needle base 154, and removes the inner needle 152 from the insertion needle body 151. After removing the inner needle 152, a syringe or the like is attached to the outer needle base 154 to inject a drug, such as anesthetics. Alternatively, a biopsy sample is sampled from the point of the subject where the insertion needle 15 has been inserted.

Figure 3:
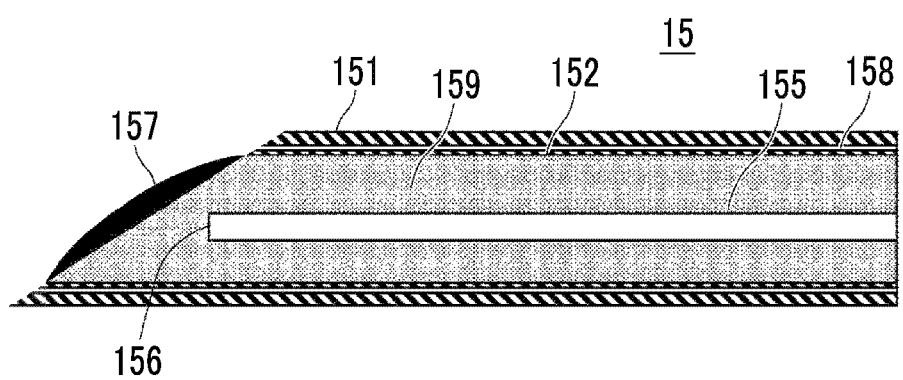
FIG. 3 is a cross-sectional view showing the vicinity of the distal end of the insertion needle.

FIG. 3 shows a cross section near the distal end of the insertion needle 15. The inner needle 152 includes a light guide member 155, a light absorption member 157, a tube 158, and a transparent resin 159. The tube 158 is a hollow tube formed of polyimide, for example. The tube 158 may be a metal tube formed of stainless steel. The outer diameter of the tube 158 is slightly smaller than the diameter of the inner cavity of the insertion needle body 151. The transparent resin 159 is disposed in the tube 158. For example, an epoxy resin (adhesive) is used as the transparent resin 159. The tube 158 and the transparent resin 159 are cut at an acute angle similar to the insertion needle tip formed at an acute angle. The transparent resin 159 may clog at least a distal end portion of the tube 158, and it does not necessarily need to clog the entire inside of the tube 158. As the transparent resin 159, a photocurable resin, a thermally curable resin, or a room temperature curable resin can be used.

Light guided by the optical fiber 16 (refer to FIG. 1) is incident on the light guide member 155 in the inner needle 152 from the optical connector provided in the inner needle base 153. Instead of providing the optical connector in the inner needle base 153, the optical fiber 16 itself may be used as the light guide member 155. The light guide member 155 guides the light emitted from the laser unit 13 in the vicinity of the opening of the insertion needle. The light guided by the light guide member 155 is emitted from a light emitting portion 156 provided in the vicinity of the opening. The light guide member 155 is formed of, for example, an optical fiber, and the end surface of the optical fiber on the light traveling side when viewed from the laser unit 13 forms the light emitting portion 156. For example, laser light of 0.2 mJ is emitted from the light emitting portion 156.

The light guide member 155 is embedded into the tube 158 by the transparent resin 159. The light absorption member 157 that is a photoacoustic wave generating portion is disposed at the distal end of the tube 158, and the light emitted from the light emitting portion 156 is emitted to the light absorption member 157. Due to the absorption of the emitted light by the light absorption member 157, a photoacoustic wave is generated at the distal end of the insertion needle. Since the light absorption member 157 is present at the distal end of the insertion needle 15, it is possible to generate a photoacoustic wave at one point of the distal end of the insertion needle 15. Since the length of a photoacoustic wave generation source (sound source) is sufficiently shorter than the length of the entire insertion needle, the sound source can be regarded as a point source. As the light absorption member 157, for example, an epoxy resin containing black pigment mixed thereinto, a polyurethane resin, a fluorine resin, or silicone rubber can be used. Alternatively, a metal or oxide having a light absorption property with respect to the wavelength of laser light may be used as the light absorption member 157. For example, oxides, such as an iron oxide, a chromium oxide, and a manganese oxide having a high light absorption property with respect to the wavelength of laser light, can be used as the light absorption member 157. Alternatively, a metal, such as Ti or Pt, may be used as the light absorption member 157.

The inner needle 152 can be manufactured in the following procedure. First, the transparent resin 159 before curing is injected into the tube 158. Then, the light guide member 155 is inserted into the tube 158, and is positioned such that the light emitting end of the light guide member 155 forming the light emitting portion 156 is disposed in the vicinity of the tube 158. In this positioning, the position may be adjusted such that the light emitting end is disposed at the distal end of the tube 158 by observing the light guide member 155 using a microscope, for example. Here, "vicinity" refers to a position where it is possible to generate photoacoustic waves capable of imaging the position of the distal end of the insertion needle 15 with accuracy, which is required for insertion work in the light absorption member 157 disposed at the distal end, in a case where the light emitting portion 156 is disposed at the position. For example, "vicinity" is the range of 0 mm to 3 mm toward the proximal end side from the distal end of the insertion needle 15. Since the transparent resin 159 is transparent, it is possible to check the position of the light emitting end of the light guide member 155 during adjustment. Instead of the above, the light guide member 155 may be inserted first, and the transparent resin 159 may be injected thereafter.

After positioning, the transparent resin 159 is cured by heat curing in a state in which the light guide member 155 has been inserted into the tube 158. Then, the distal ends of the tube 158 and the transparent resin 159 are cut at an acute angle so as to have a shape suitable for the distal end of the insertion needle body 151. Then, the resin having a light absorption property that forms the light absorption member 157 is applied to cover at least a part of the cut surface, and the resin is cured by heat curing, for example.

In the above, the light guide member 155 is inserted into the tube 158 and the position is adjusted, and the transparent resin is cured and is then cut at an acute angle. However, the invention is not limited thereto. The tube may be cut at an acute angle first, the light guide member 155 may be inserted into the tube and the position may be adjusted, and the transparent resin may be cured. In this case, a metal tube formed of stainless steel may be used as the tube.

Referring back to FIG. 1, a probe 11 is an acoustic wave detection unit, and has a plurality of detector elements (ultrasound transducers) arranged in a one-dimensional manner. The probe 11 detects photoacoustic waves generated from the light absorption member 157 (refer to FIG. 3) after the insertion needle 15 is inserted into the subject. In addition to the detection of photoacoustic waves, the probe 11 performs transmission of acoustic waves (ultrasound waves) to the subject and reception of reflected acoustic waves (reflected ultrasound waves) of the transmitted ultrasound waves. The probe 11 is not limited to the linear probe, but may be a convex probe or a sector probe.

The ultrasound unit 12 has a receiving circuit 21, an analog/digital (AD) conversion unit 22, a data separation unit 24, a photoacoustic image generation unit 25, an ultrasound image generation unit 26, an image combining unit 27, a control unit 28, a transmission control circuit 29, a sound source position detection unit 30, a first signal acquisition unit 31, a second signal acquisition unit 32, and a light emission control unit 33. The ultrasound unit 12 forms a signal processing device.

The receiving circuit 21 receives a detection signal of the photoacoustic wave detected by the probe 11. In addition, the detection signal of the reflected ultrasound wave detected by the probe 11 is received. The AD conversion unit 22 converts the detection signals of the photoacoustic wave and the reflected ultrasound wave, which have been received by the receiving circuit 21, into digital signals. The AD conversion unit 22 samples the detection signals of the photoacoustic wave and the reflected ultrasound wave based on a sampling clock signal, for example.

Detection signals (sampling data) of the photoacoustic wave and the reflected ultrasound wave, which have been sampled by the AD conversion unit 22, are input to the data separation unit 24. The data separation unit 24 inputs the sampling data of the detection signal of the photoacoustic wave to the photoacoustic image generation unit 25. In addition, the sampling data of the reflected ultrasound wave is input to the ultrasound image generation unit (a reflected acoustic wave image generation unit) 26.

The photoacoustic image generation unit 25 generates a photoacoustic image based on the detection signal of the photoacoustic wave detected by the probe 11. The generation of a photoacoustic image includes, for example, image reconstruction such as phase matching addition, detection, and logarithmic conversion. The photoacoustic image generation unit 25 can generate a photoacoustic image by at least adding the detection signals of a plurality of photoacoustic waves. Since it is necessary to make the laser unit 13 emit light once for one photoacoustic wave detection, the number of light emissions per one image generation and the number of additions of the detection signal of the photoacoustic wave are synonymous.

The ultrasound image generation unit 26 generates an ultrasound image (reflected acoustic wave image) based on the detection signal of the reflected ultrasound wave detected by the probe 11. The generation of an ultrasound image also includes image reconstruction such as phase matching addition, detection, and logarithmic conversion. The image combining unit 27 combines the photoacoustic image and the ultrasound image. The composite image obtained by the image combining unit 27 is displayed on the screen of the image display unit 14, such as a display device. The photoacoustic image generation unit 25 and the ultrasound image generation unit 26 repeatedly generate the photoacoustic image and the ultrasound image, respectively. The number of photoacoustic images generated per unit time and the number of ultrasound images generated per unit time are the same.

The control unit 28 controls each unit in the ultrasound unit 12. For example, the control unit 28 transmits a trigger signal to the laser unit 13 so that the laser unit 13 emits laser light. In addition, the control unit 28 controls the sampling start timing of the photoacoustic wave by transmitting a sampling trigger signal to the AD conversion unit 22 in response to the emission of the laser light. The area where the photoacoustic wave is to be detected may be divided into a plurality of areas. In this case, emission of light to the subject and detection of a photoacoustic wave are performed in each area.

In the case of acquiring an ultrasound image, the control unit 28 transmits an ultrasound wave transmission trigger signal for giving an instruction of ultrasound wave transmission to the transmission control circuit 29. When the ultrasound wave transmission trigger signal is received, the transmission control circuit 29 makes the probe 11 transmit ultrasound waves. The probe 11 detects reflected ultrasound waves by performing a scan while shifting the acoustic line by one line at a time. The control unit 28 transmits a sampling trigger signal to the AD conversion unit 22 according to the timing of ultrasound wave transmission, thereby starting the sampling of reflected ultrasound waves.

The sound source position detection unit 30 detects the position of the photoacoustic wave generating source from the photoacoustic image generated by the photoacoustic image generation unit 25. For example, the sound source position detection unit 30 detects a position of a pixel having a maximum pixel value in the photoacoustic image as the position of the photoacoustic wave generating source. The position of the photoacoustic wave generating source corresponds to the position of the light absorption member 157 (refer to FIG. 3) of the insertion needle 15. The sound source position detection unit 30 may detect the position of the photoacoustic wave generating source at a position deeper than the depth position set in advance. For example, the sound source position detection unit 30 excludes a shallow region where the depth position is shallower than 2 mm, and detects the position of the photoacoustic wave generating source in a region where the depth position is 2 mm or more. This is because it is thought that the insertion needle 15 is not inserted into such a shallow region and that the influence of artifacts on the probe 11 is large at the shallow position and accordingly it is not possible to correctly detect the position of the photoacoustic wave generating source.

The first signal acquisition unit 31 acquires a first signal value indicating the intensity of the photoacoustic wave emitted from the photoacoustic wave generating source. Hereinafter, the first signal value is also referred to as an S value. The first signal acquisition unit 31 acquires the pixel value of a pixel of a photoacoustic image, which corresponds to the position of the photoacoustic wave generating source, as the S value, for example. Alternatively, the signal value of a detection signal of the photoacoustic wave before imaging may be acquired as the S value.

The second signal acquisition unit 32 acquires a signal value indicating noise in a photoacoustic image as a second signal value. Hereinafter, the second signal value is also referred to as an N value. The second signal acquisition unit 32 calculates a variance of the pixel values of photoacoustic images corresponding to a plurality of positions around the position of the photoacoustic wave generating source, for example. Alternatively, a variance of the signal values of the detection signals of photoacoustic waves before imaging is calculated. The second signal acquisition unit 32 calculates, for example, a variance of the pixel values of photoacoustic images of a plurality of positions, which are included in the range of a predetermined distance from the position of the photoacoustic wave generating source, or a variance of the signal values of the detection signals of photoacoustic waves. The second signal acquisition unit 32 acquires the value of the acquired variance as the N value.

Incidentally, in a case where a large amount of noise is included in the detection signal of the photoacoustic wave, a large amount of noise is also included in the S value acquired by the first signal acquisition unit 31. The first signal acquisition unit 31 may calculate an average value of pixel values or an average value of signal values, which correspond to a plurality of positions around the position of the photoacoustic wave generating source, as a background value, and may acquire a value, which is obtained by subtracting the background value from the pixel value or the signal value of a pixel of the photoacoustic image corresponding to the position of the photoacoustic wave generating source, as the S value. The region where the background value is to be calculated is the same as the range (region) of the pixel position where the second signal acquisition unit 32 acquires the second signal value. The processing of subtracting the background value may be performed when the pixel value or the signal value corresponding to the position of the photoacoustic wave generating source is approximately equal to the background value, for example, when the pixel value or the signal value corresponding to the position of the photoacoustic wave generating source is equal to or less than twice the background value.

The light emission control unit 33 controls the number of light emissions and the light emission interval of the laser unit 13 for one photoacoustic image generation. The light emission control unit 33 controls the number of light emissions and the light emission interval based on the ratio between the S value and the N value, specifically, based on a value obtained by dividing the S value by the N value. The light emission control unit 33 makes the laser unit 13 emit light at equal intervals, for example, through the control unit 28, until the generation of the next photoacoustic image after the generation of one photoacoustic image. After the photoacoustic image is generated, the number of light emissions and the light emission interval of the laser unit 13 when generating the next photoacoustic image are determined based on the relative magnitude relationship between the S value and the N value that are acquired from the generated photoacoustic image.

For example, in the generation of an ultrasound image, the probe 11 performs transmission of the ultrasound wave and detection of the reflected ultrasound wave by performing a scan while shifting the acoustic line by one line at a time. In this case, the light emission control unit 33 may make the laser unit 13 emit light between scans of acoustic lines. For example, when transmission of the ultrasound wave and detection of the reflected ultrasound wave may be performed first, and the photoacoustic wave may be detected by emitting the light from the laser unit 13 when the scanning position of the acoustic line becomes a specific scanning position. The light emission control unit 33 controls the emission of the laser unit 13 with reference to a look-up table in which the number of light emissions is associated with the emission timing for determining between which scanning positions in the detection of reflected ultrasound waves each emission is to be performed, for example.

The value obtained by dividing the S value by the N value corresponds to the signal-to-noise ratio (SN ratio). In general, it is possible to increase the SN ratio by increasing the number of additions. In other words, it is possible to improve the image quality of the photoacoustic image by increasing the number of light emissions of the laser unit 13 for one photoacoustic image generation. In the present embodiment, not only the number of light emissions but also the light emission interval is controlled. The time required for multiple detections of photoacoustic waves is proportional to the product of the number of light emissions and the light emission interval. In a case where only the number of light emissions is simply increased without changing the light emission interval, the time required for the detection of photoacoustic waves is increased by the amount of increase. Accordingly, the number of photoacoustic images generated per unit time is reduced. By increasing or decreasing the light emission interval according to the number of light emissions, it is possible to improve the image quality of the photoacoustic image without reducing the number of photoacoustic images generated per unit time.

The light emission control unit 33 determines the number of light emissions such that the SN ratio falls within a predetermined target range. The S value is proportional to the square root of the number of light emissions. The target range may be determined in advance as a set value of the apparatus, or a slider or the like may be displayed on the display screen of the image display unit 14 so that the target range can be arbitrarily set by the user.

When the SN ratio is smaller than a first threshold value that is the lower limit of the target range, the light emission control unit 33 makes the number of light emissions of the laser unit 13 larger than the current number of light emissions and makes the light emission interval shorter than the current light emission interval. By increasing the number of light emissions and increasing the number of detection signals of photoacoustic waves to be added up, it is possible to improve the image quality. At this time, by shortening the light emission interval, it is possible to prevent the time required for multiple detections of photoacoustic waves from becoming too long. Therefore, it is possible to suppress an increase in processing time due to increasing the number of additions. For example, when setting the number of light emissions at the time of generation of the next photoacoustic image to twice the current number of light emissions, the light emission control unit 33 sets the light emission interval at the time of generation of the next photoacoustic image to half of the current light emission interval. In this case, it is possible to increase the number of additions while maintaining the time required for multiple detections of photoacoustic waves constant.

When the SN ratio is larger than a second threshold value that is the upper limit of the target range, the light emission control unit 33 makes the number of light emissions of the laser unit 13 smaller than the current number of light emissions and makes the light emission interval longer than the current light emission interval. The photoacoustic image is used to check the position of the insertion needle 15. Accordingly, since the position of the photoacoustic wave generating source, that is, the position of the needle tip of the insertion needle 15, is checked by the photoacoustic image, an excessively high SN ratio is not required for the photoacoustic image. By reducing the number of light emissions of the laser unit 13 when the SN ratio is larger than the second threshold value, it is possible to suppress the generation of a photoacoustic image having an excessively high SN ratio. Reducing the number of light emissions is advantageous from the viewpoint of lifetime of the laser unit 13.

Figure 4:
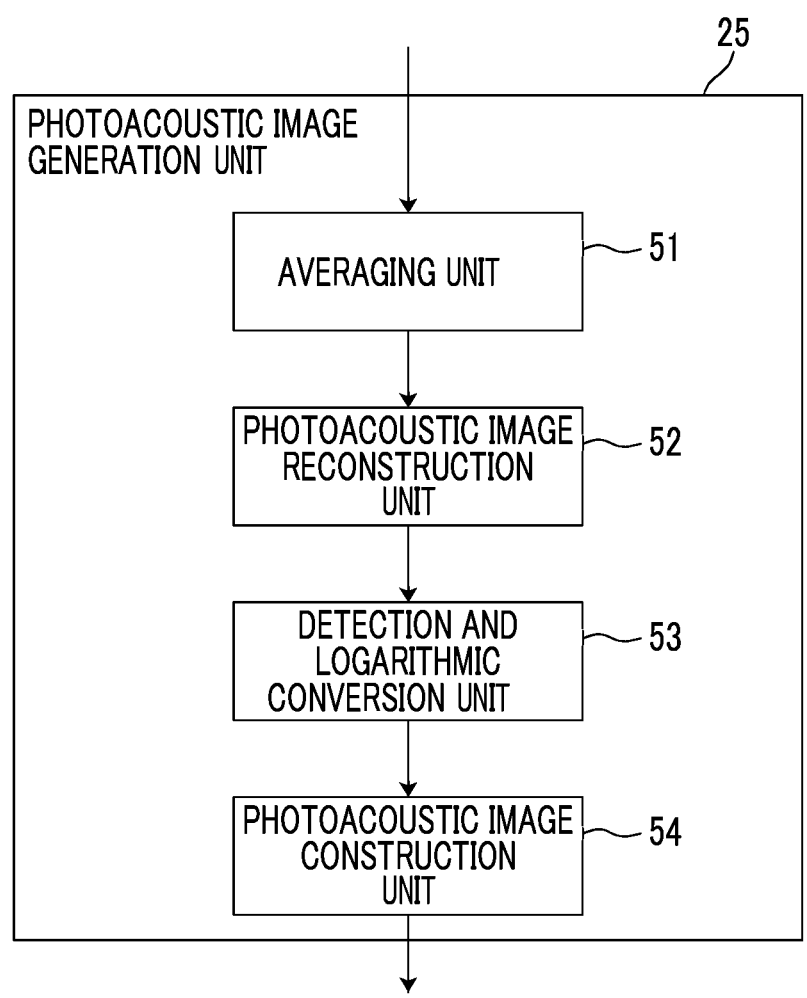
FIG. 4 is a block diagram showing a photoacoustic image generation unit.

FIG. 4 shows the photoacoustic image generation unit 25. The photoacoustic image generation unit 25 has an averaging unit 51, a photoacoustic image reconstruction unit 52, detection and a logarithmic conversion unit 53, and a photoacoustic image construction unit 54. The averaging unit 51 performs averaging of the detection signals of a plurality of photoacoustic waves. Instead of averaging, only addition may be performed. For example, if the number of light emissions of the laser unit 13 per one photoacoustic image generation is four times, the averaging unit 51 adds up the detection signals of photoacoustic waves corresponding to the four times and averages the result.

The photoacoustic image reconstruction unit 52 reconstructs the detection signal of the photoacoustic wave obtained by the averaging. The photoacoustic image reconstruction unit 52 performs reconstruction using a Fourier transform method (FTA method). Instead of the Fourier transform method, reconstruction may be performed using a delay addition method or a circular back projection (CBP). The reconstructed detection signal of the photoacoustic wave can be regarded as a photoacoustic image.

The detection and logarithmic conversion unit 53 obtains an envelope of the detection signal of the photoacoustic wave reconstructed by the photoacoustic image reconstruction unit 52, and performs logarithmic conversion for the obtained envelope. The photoacoustic image construction unit 54 generates a photoacoustic image based on the detection signal of the photoacoustic wave of each line after the logarithmic conversion has been performed. The photoacoustic image construction unit 54 converts a photoacoustic image by converting the position in the time axis direction of the detection signal (peak portion) of the photoacoustic wave into the position in the depth direction in a photoacoustic layer image, for example.

Figure 5:
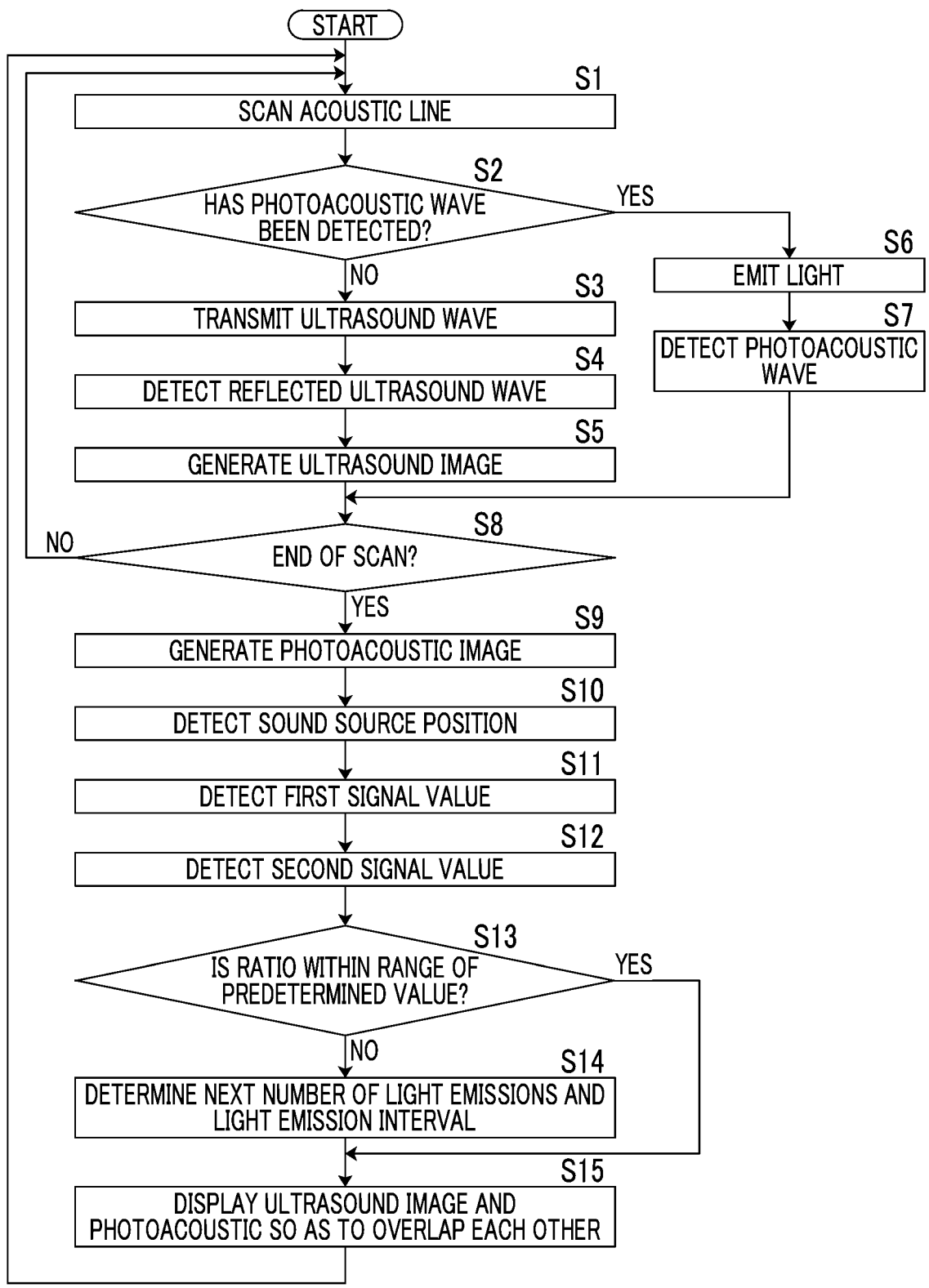
FIG. 5 is a flowchart showing the operation procedure of the photoacoustic image generation apparatus.

Subsequently, the operation procedure will be described. FIG. 5 shows the operation procedure of the photoacoustic image generation apparatus 10. The control unit 28 starts a scan of the acoustic line (step S1). The control unit 28 determines whether or not to perform the detection of a photoacoustic wave (step S2). The control unit 28 determines whether or not to perform the detection of a photoacoustic wave, for example, based on the scanning position of the acoustic line. At which scanning position the detection of a photoacoustic wave is to be performed is designated by the light emission control unit 33. Alternatively, information regarding the number of light emissions and the light emission interval may be transmitted to the control unit 28 from the light emission control unit 33, and the control unit 28 may determine at which scanning position the detection of a photoacoustic wave is to be performed.

In a case where the detection of a photoacoustic wave is not performed, the control unit 28 transmits an ultrasound trigger signal to the transmission control circuit 29. The transmission control circuit 29 makes the probe 11 transmit an ultrasound wave in response to the ultrasound trigger signal (step S3). The probe 11 detects a reflected ultrasound wave after the transmission of an ultrasound wave (step S4). The probe 11 transmits ultrasound waves, for example, from 64 detector elements, and detects reflected ultrasound waves by the 64 detector elements. In addition, transmission and reception of ultrasound waves may be performed at separate positions. For example, ultrasound waves may be transmitted from a position different from the probe 11, and reflected ultrasound waves of the transmitted ultrasound waves may be received by the probe 11.

The reflected ultrasound waves detected by the probe 11 are input to the AD conversion unit 22 through the receiving circuit 21. The AD conversion unit 22 samples detection signals of the reflected ultrasound waves. The ultrasound image generation unit 26 receives sampling data of the detection signals of the reflected ultrasound waves through the data separation unit 24, and generates an ultrasound image (step S5). The ultrasound image generation unit 26 generates an ultrasound image of one acoustic line by performing delay addition of the sampling data of the detection signals of the reflected ultrasound waves for 64 elements, for example.

In a case where it is determined that the detection of a photoacoustic wave is performed in step S2, the control unit 28 transmits a trigger signal to the laser unit 13. When the trigger signal is received, the laser unit 13 starts laser oscillation to emit pulsed laser light (step S6). The pulsed laser light emitted from the laser unit 13 is guided to the vicinity of the distal end of the insertion needle 15 by the light guide member 155 (refer to FIG. 3), and is emitted from the light emitting portion 156. As a result, at least some of the pulsed laser light beams are emitted to the light absorption member 157 disposed at the distal end of the insertion needle 15.

The probe 11 detects photoacoustic waves generated by the emission of the laser light, that is, photoacoustic waves emitted from the light absorption member 157 (step S7). The AD conversion unit 22 receives detection signals of the photoacoustic waves through the receiving circuit 21, and samples the detection signals of the photoacoustic waves. The sampling data of the detection signals of the photoacoustic waves is transmitted to the photoacoustic image generation unit 25 through the data separation unit 24. The averaging unit 51 (refer to FIG. 4) of the photoacoustic image generation unit 25 adds up the detection signals of the photoacoustic waves by adding the detection signal of the current photoacoustic wave to the addition result of the detection signals of the photoacoustic waves up to now in a memory region, which is secured for detection signals of photoacoustic waves, whenever the detection of a photoacoustic wave is performed, for example. Alternatively, it is also possible to store the detection signal of a photoacoustic wave of each time in a memory region and to calculate the sum of the detection signals of photoacoustic waves of respective times after the end of the detection of photoacoustic waves corresponding to the number of light emissions.

Here, the reflected ultrasound wave transmitted from the probe 11 propagates back and forth between the probe 11 and the ultrasound wave reflection position, while the photoacoustic wave propagates through one way from the vicinity of the distal end of the insertion needle 15, which is the generation position, to the probe 11. Accordingly, the detection of the reflected ultrasound wave requires twice the time for the detection of the photoacoustic wave generated at the same depth position. The sampling time of the AD conversion unit 22 at the time of photoacoustic wave sampling may be set to half of the sampling time at the time of reflected ultrasound wave sampling. Specifically, when the sampling time of the reflected ultrasound wave is 160 microseconds, the sampling time of the photoacoustic wave may be 80 microseconds.

The control unit 28 determines whether or not the scanning of the acoustic line has ended (step S8). If the scanning has not ended, the process returns to step S1 to move the scanning position by one scanning position from the scanning position where the detection of the reflected ultrasound wave has been performed last. The photoacoustic image generation apparatus 10 repeatedly performs the processing from step S1 to step S8 until the scanning of the acoustic line is completed. When the area for detecting a photoacoustic wave is divided into a plurality of areas, light emission and photoacoustic wave detection for the subject are performed in each area. Accordingly, the total number of light emissions is a product of the number of divisions of the area and the number of light emissions in each area. Detection of a photoacoustic wave may be performed continuously in the same area, and movement to the next area may be performed if the detection signals of photoacoustic waves corresponding to the number of light emissions are obtained.

If it is determined that the scanning of the acoustic line has ended in step S8, the photoacoustic image generation unit 25 generates a photoacoustic image based on the detection signals of the photoacoustic waves corresponding to the number of light emissions that have been added up (step S9). The sound source position detection unit 30 detects the position of the photoacoustic wave generating source from the photoacoustic image (step S10). For example, the sound source position detection unit 30 detects a position of a pixel having highest brightness (maximum pixel value) in the photoacoustic image as the position of the photoacoustic wave generating source.

The first signal acquisition unit 31 acquires the pixel value of the pixel of the photoacoustic image corresponding to the position of the photoacoustic wave generating source as the S value (step S11). The second signal acquisition unit 32 calculates, for example, a variance of the pixel values of photoacoustic images of a plurality of positions, which are included in the range of a predetermined distance from the position of the photoacoustic wave generating source, or a variance of the signal values of the detection signals of photoacoustic waves, and acquires the value of the calculated variance as the N value (step S12).

The light emission control unit 33 calculates a ratio between the S value and the N value, and determines whether or not the calculated ratio is within a predetermined range (step S13). Specifically, it is determined whether or not the ratio between the S value and the N value is the first threshold value or more and the second threshold value or less. When the ratio is smaller than the first threshold value or when the ratio is larger than the second threshold value, the light emission control unit 33 changes the number of light emissions and the light emission interval of the laser unit 13 at the time of the next photoacoustic image generation from the current number of light emissions and the current light emission interval (step S14). When the ratio between the S value and the N value is smaller than the first threshold value, the light emission control unit 33 increases the number of light emissions and the light emission interval of the laser unit 13 from the current number of light emissions and the current light emission interval. When the ratio between the S value and the N value is larger than the second threshold value, the light emission control unit 33 reduces the number of light emissions and the light emission interval of the laser unit 13 from the current number of light emissions and the current light emission interval. When the ratio between the S value and the N value is the first threshold value or more and the second threshold value or less, the number of light emissions and the light emission interval are not changed.

The image combining unit 27 displays an ultrasound image and a photoacoustic image on the image display unit 14 so as to overlap each other (step S15). The position of the photoacoustic wave generating source detected by the sound source position detection unit 30 may be displayed on the image display unit 14. In this case, the photoacoustic image may be replaced with an image showing the position of the photoacoustic wave generating source, and the image and the ultrasound image may be displayed on the image display unit 14 so as to overlap each other. A portion of the ultrasound image within a predetermined distance from the position of the photoacoustic wave generating source detected by the sound source position detection unit 30 may be displayed in an enlarged manner. The portion may be an image having improved spatial resolution and contrast resolution. For example, not only reception phasing addition to perform the correction of reception delay but also transmission phasing addition to perform the correction of transmission delay may be performed for the region within the predetermined distance from the photoacoustic wave generating source, and the spatial resolution and the contrast resolution may be improved around the photoacoustic wave generating source. The display of an image and the processing from step S10 to S14 may be performed in parallel. After the image display, the process returns to step S1 to continue the generation of an ultrasound image and the generation of a photoacoustic image.

Figures 6, 7:
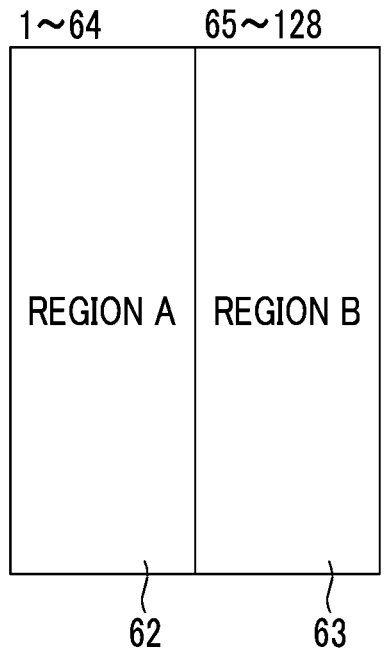
FIG. 6 is a diagram showing the division of an area to detect a photoacoustic wave.
FIG. 7 is a table showing the correspondence among the magnification of the SN ratio, the number of light emissions, and the light emission interval.

FIG. 6 shows the division of an area to detect a photoacoustic wave. For example, it is assumed that the number of detector elements provided in the probe 11 is 128 and the AD conversion unit 22 can sample the signals of 64 elements at a time. An ultrasound image is generated, for example, by scanning the acoustic line while shifting the ultrasound transducer connected to the AD conversion unit 22 by one element at a time to reconstruct one line at a time. By reconstructing the reflected ultrasound wave signals detected by 64 detector elements for each line, image data for one line is obtained. In addition, at the end, reflected ultrasound wave signals detected by detector elements, the number of which is smaller than 64, are reconstructed.

For the photoacoustic image, a total of 128 elements are divided into two areas (64 elements per area), and light emission and photoacoustic wave detection are performed in each area. A region A 62 shown in FIG. 6 is a region corresponding to the first to 64th detector elements, and a region B 63 is a region corresponding to the 65th to 128th detector elements. For example, when the number of additions of photoacoustic waves is four times, that is, when the number of light emissions in each area is four times, light emission is performed four times in the region A 62, and detection signals of photoacoustic waves corresponding to the four times, which have been detected by the first to 64th detector elements, are added up. In addition, light emission is performed four times in the region B 63, and detection signals of photoacoustic waves corresponding to the four times, which have been detected by the 65th to 128th detector elements, are added up.

FIG. 7 shows the correspondence among the magnification of the SN ratio (SN magnification), the number of light emissions, and the light emission interval. In FIG. 7, "SN magnification" indicates the magnification of the ratio between the S value and the N value when the ratio between the S value and the N value in the case of performing no averaging is set to 1. The "number of light emissions" indicates the number of light emissions in each area, and "sum of light emissions" indicates the number of light emissions×the number of areas. "First line position" indicates the position of the acoustic line where light emission and detection of a photoacoustic wave are performed first, and "line interval" indicates an interval between acoustic lines up to the next light emission and detection of a photoacoustic wave.

For example, when it is necessary to double the SN magnification in a case where the number of light emissions in each area is once currently, that is, there is no averaging, it is preferable to increase the number of light emissions in each area four times. Assuming that an area to detect a photoacoustic wave is divided into two areas, the total number of light emissions is eight times. In order to perform a total of eight times of light emission and photoacoustic wave detection while scanning the acoustic lines for 128 elements for the detection of reflected ultrasound waves, it is preferable to perform the first light emission and photoacoustic wave detection after scanning the eighth acoustic line and then perform light emission and photoacoustic wave detection at 16-line intervals. That is, it is preferable to perform the first light emission and photoacoustic wave detection after performing a scan up to the eighth acoustic line and then perform light emission and photoacoustic wave detection each time 16-line acoustic lines are scanned.

For example, transmission of ultrasound waves and detection of reflected ultrasound waves are started from the first line of the probe 11, and the range of detector elements (opening elements) for performing the transmission of ultrasound waves and the detection of reflected ultrasound waves is shifted by one line at a time. Between the detection of reflected ultrasound waves in the eighth line and the detection of reflected ultrasound waves in the ninth line, first light emission and photoacoustic wave detection for the subject are performed in the region A 62. Then, between the detection of reflected ultrasound waves in the 24th line and the detection of reflected ultrasound waves in the 25th line, second light emission and photoacoustic wave detection for the subject are performed in the region A 62. Between the detection of reflected ultrasound waves in the 40th line and the detection of reflected ultrasound waves in the 41th line, third light emission and photoacoustic wave detection for the subject are performed in the region A 62. Between the detection of reflected ultrasound waves in the 56th line and the detection of reflected ultrasound waves in the 57th line, fourth light emission and photoacoustic wave detection for the subject are performed in the region A 62.

After performing light emission and photoacoustic wave detection four times in the region A 62, first light emission and photoacoustic wave detection for the subject are performed in the region B 63 between the detection of reflected ultrasound waves in the 72th line and the detection of reflected ultrasound waves in the 73th line. Then, between the detection of reflected ultrasound waves in the 88th line and the detection of reflected ultrasound waves in the 89th line, second light emission and photoacoustic wave detection for the subject are performed in the region B 63. Between the detection of reflected ultrasound waves in the 104th line and the detection of reflected ultrasound waves in the 105th line, third light emission and photoacoustic wave detection for the subject are performed in the region B 63. Between the detection of reflected ultrasound waves in the 120th line and the detection of reflected ultrasound waves in the 121th line, fourth light emission and photoacoustic wave detection for the subject are performed in the region B 63.

In a case where the number of light emissions in each area is set to 16 times, the total number of light emissions is 32 times. In this case, it is preferable that, between the detection of reflected ultrasound waves in the second line and the detection of reflected ultrasound waves in the third line, first light emission and photoacoustic wave detection for the subject are performed in the first area. Thereafter, light emission and photoacoustic wave detection for the subject are performed in the first area every four acoustic lines. After performing the light emission 16 times for the first area, movement to the second area is made. Also in the second area, light emission and photoacoustic wave detection for the subject may be performed every four acoustic lines.

Figure 8:
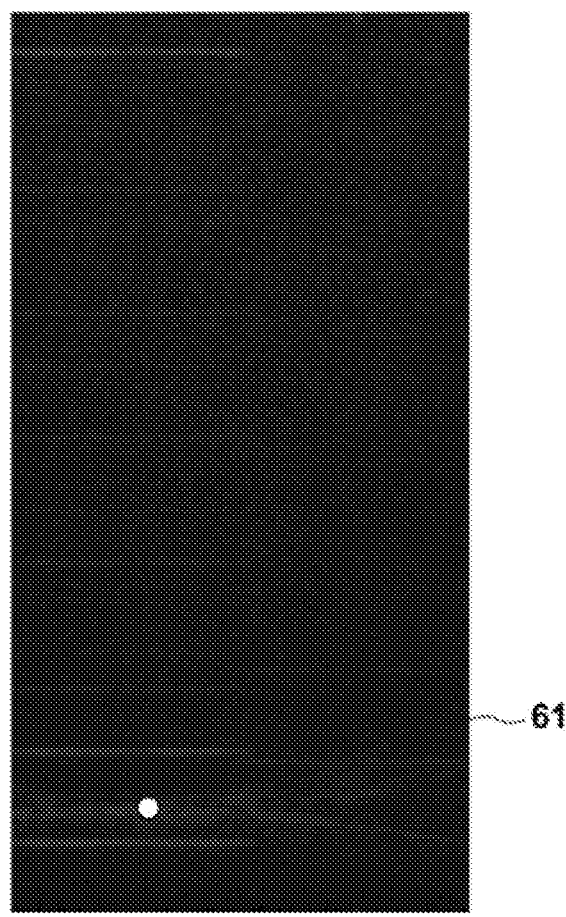
FIG. 8 is a diagram showing an image example of a generated photoacoustic image.

FIG. 8 shows an image example of a generated photoacoustic image. The horizontal direction of the image corresponds to the arrangement direction of detector elements, and the vertical direction of the image corresponds to the depth direction. By the photoacoustic image, for example, the range up to 8 cm in the depth direction from the ultrasound detection surface of the probe 11 is imaged. The photoacoustic image shown in FIG. 8 is obtained by inserting the insertion needle 15 into a container filled with water, emitting light from the laser unit 13 to generate photoacoustic waves in the insertion needle 15 in water, detecting photoacoustic waves in two divided areas by the probe 11, and generating a photoacoustic image based on the detected photoacoustic waves. The diameter of the needle tip is 0.3 mm, the laser output of laser light emitted from the laser unit 13 is 2 and the wavelength is 905 nm. The number of additions of photoacoustic waves is set to one time (without averaging). The sound source position detection unit 30 detects a position (sound source position) 61 of the photoacoustic wave generating source from such a photoacoustic image.

Figure 9:
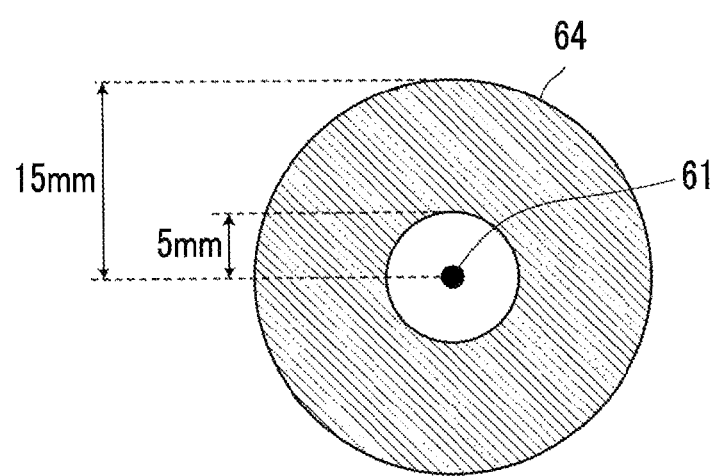
FIG. 9 is a diagram showing the position of a photoacoustic wave generating source and the region of pixels to calculate the N value.

Then, acquisition of the S value and the N value will be described in detail. FIG. 9 shows the position of a photoacoustic wave generating source and the region of pixels to calculate the N value. The first signal acquisition unit 31 acquires the signal value of the sound source position 61 as the S value. The first signal acquisition unit 31 may acquire a signal value in any stage in the image generation step as the S value. Specifically, the averaging unit 51 (refer to FIG. 4) may acquire the signal value of a detection signal of the photoacoustic wave before generating an averaged image as the S value. Alternatively, the signal value of the detection signal of the photoacoustic wave reconstructed by the photoacoustic image reconstruction unit 52 may be acquired as the S value, or the signal value after being subjected to detection and logarithmic conversion processing by the detection and logarithmic conversion unit 53 may be acquired as the S value. In addition, the pixel value of the photoacoustic image generated by the photoacoustic image construction unit 54 may be acquired as the S value.

Here, in a photoacoustic image (photoacoustic signal) before the detection is performed by the detection and logarithmic conversion unit 53 (refer to FIG. 4), the pixel value (signal value) has positive and negative values. The sound source position detection unit 30 may detect a position, at which the signal value of the photoacoustic signal before the detection is maximized or minimized, as the position of the photoacoustic wave generating source. In this case, the first signal acquisition unit 31 may acquire a so-called peak-to-peak value, which is obtained by subtracting the minimum value or the maximum value of a signal in the vicinity (for example, about two cycles) of a position where the signal value is maximized or minimized from the minimum value or the maximum value of a signal before detection, as the S value.

The second signal acquisition unit 32 acquires an N value in the vicinity excluding the sound source position 61. For example, the second signal acquisition unit 32 acquires the N value in a region away from the sound source position 61 by a predetermined distance. For example, the second signal acquisition unit 32 sets a region 64 of pixels that fall within a range of 5 mm or more and 15 mm or less from the sound source position 61, calculates a variance of the pixel values of a plurality of pixels present in the region 64, and acquires the calculated variance as the N value. It is thought that a signal present in the region 64 is a signal derived from the electrical noise of the probe. The point that a signal value in any stage in the image generation step may be acquired as the N value is the same as the case of the acquisition of the S value. In addition, the shape of the region 64 is not limited to the circular shape, and may be other shapes, for example, a rectangular shape.

Here, it is preferable to include only the signal originating from the electrical noise in a region to calculate the N value, and it is preferable that a signal due to artifacts by reconstruction or artifacts by side lobes is not included. In the photoacoustic image, artifacts by reconstruction or artifacts by side lobes are easy to come out in a direction perpendicular to the depth direction or an oblique direction. When acquiring the N value, it is preferable to exclude such a region in a specific direction where artifacts are easy to come out from calculation targets. It is preferable that the second signal acquisition unit 32 calculates a variance of the pixel values of photoacoustic images of a plurality of positions, which fall within a range of a predetermined distance from the position of the photoacoustic wave generating source and which are included in a predetermined angular range with respect to the position of the photoacoustic wave generating source, or a variance of the signal values of the detection signals of photoacoustic waves.

Figure 10:
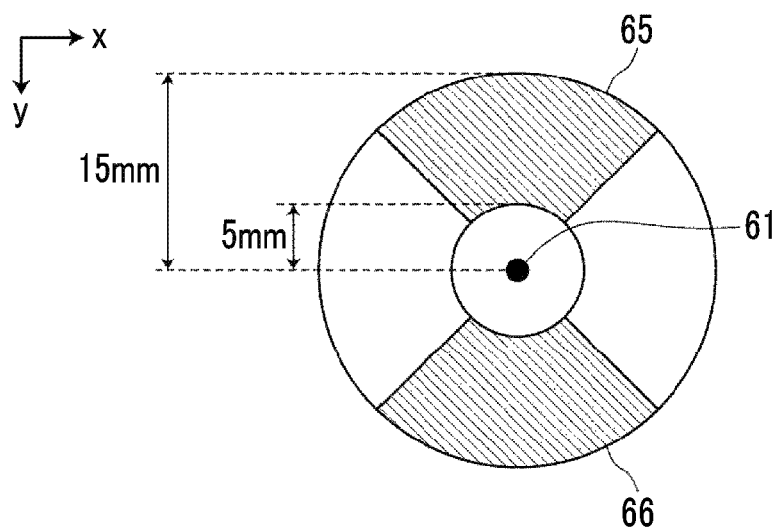
FIG. 10 is a diagram showing another example of the position of the photoacoustic wave generating source and the region of pixels to calculate the N value.

FIG. 10 shows another example of the position of a photoacoustic wave generating source and the region of pixels to calculate the N value. The second signal acquisition unit 32 may set regions on both sides in a depth direction (in FIG. 10, y direction) with respect to the sound source position 61, in a region away from the sound source position 61 by a predetermined distance, may be set as regions of pixels to calculate the N value, for example. Specifically, as shown in FIG. 10, if the shape of a region is a circle, in a region of pixels included in the range of a distance of 5 mm or more and 15 mm or less from the sound source position 61, regions 65 and 66 that are included in the angular range of −45° C. or more and 45° C. or less with a direction (depth direction) perpendicular to the ultrasound detection surface of the probe 11 as 0° C. may be set as calculation target regions. By excluding the region in a direction (in FIG. 10, x direction) perpendicular to the depth direction, in which artifacts are easy to come out, from calculation targets, it is possible to acquire the N value from the signal derived from the electrical noise. By limiting the region to calculate the N value in this manner, it is possible to improve the calculation accuracy. In addition, it is possible to improve the calculation speed.

Figure 11:
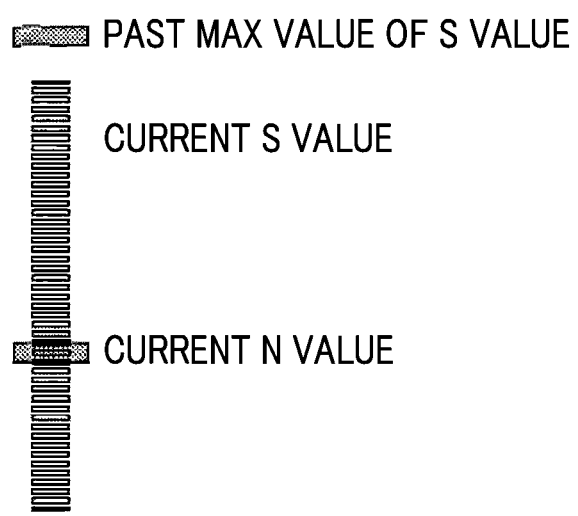
FIG. 11 is a diagram showing a display example of the S value and the N value.

During image display, the S value and the N value may be displayed in addition to the ultrasound image and the photoacoustic image. FIG. 11 shows a display example of the S value and the N value. For example, an indicator showing the current S value may be displayed together with the ultrasound image and the photoacoustic image, so that the detection intensity of the photoacoustic wave generated in the insertion needle 15 can be seen. A maximum value of the S value in a predetermined time, for example, in a second may be displayed by the indicator. When changing the angle of the probe 11 with respect to the subject, the S value is maximized when there is a photoacoustic wave generating source in a direction perpendicular to the ultrasound detection surface of the probe 11. Therefore, the maximum value of the past S value can be an indicator when searching for a direction in which the position of the photoacoustic wave generating source is present. In addition, the N value may be displayed by the indicator. In this case, it is possible to know the noise level for the S value by referring to the indicator.

In the present embodiment, a photoacoustic image is generated, the signal value at the position of the photoacoustic image generating source is acquired as the S value, and a signal value indicating noise in the photoacoustic image is acquired as the N value. The light emission control unit 33 controls the number of light emissions and the light emission interval of the laser unit 13 for one photoacoustic image generation based on the ratio between the S value and the N value. By generating a photoacoustic image by at least adding up the detection signals of photoacoustic waves corresponding to the number of light emissions, it is possible to improve the SN ratio. Therefore, it is possible to improve the image quality of the photoacoustic image. In particular, in the present embodiment, the light emission interval is controlled in accordance with the number of light emissions. When increasing or decreasing the number of light emissions, by decreasing or increasing the light emission interval according to the increase or decrease in the number of light emissions, it is possible to improve the image quality of the photoacoustic image without reducing the number of photoacoustic images generated per unit time.

In the present embodiment, since it is possible to check the position of the insertion needle 15 using a photoacoustic image, an excessive S value in the photoacoustic image is not necessary. When the SN ratio is high more than necessary, it is possible to drive the laser unit 13 to the extent to secure the SN ratio, which is required to check the position of the insertion needle 15, by reducing the number of light emissions and extending the light emission interval. It is possible to reduce the power consumption of the laser unit 13 by causing the laser unit 13 not to wastefully emit light. In addition, it is also possible to extend the life of the laser unit 13.

Here, changing the number of times of averaging based on the SN ratio is disclosed in JP2011-229815A. In JP2011-229815A, however, the number of additions is changed, but the light emission interval of the light source is not changed. Accordingly, the number of photoacoustic images generated per unit time decreases as the number of additions increases. For example, in the case of originally generating a photoacoustic image without averaging so that an ultrasound image and a photoacoustic image are generated at a rate of one to one, if the number of times of the averaging of photoacoustic images is changed to four times, only one photoacoustic image can be generated while generating four ultrasound images. Accordingly, the real-time characteristics of the photoacoustic image are reduced. In contrast, in the present embodiment, for example, by halving the light emission interval when the number of light emissions (the number of additions) is doubled, it is possible to obtain a photoacoustic image that has an improved SN ratio without reducing the number of photoacoustic images generated per unit.

Figure 12:
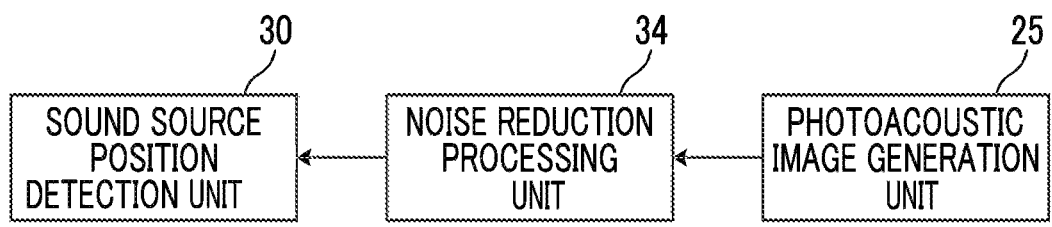
FIG. 12 is a block diagram showing a part of the configuration of a photoacoustic image generation apparatus in the case of detecting the position of a photoacoustic wave generating source from a photoacoustic image after noise reduction.

If a large amount of noise is included in a photoacoustic image, it is conceivable that it is difficult to correctly detect the position of the photoacoustic wave generating source. In order to improve the detection accuracy of the position of the photoacoustic wave generating source, processing for reducing noise from the photoacoustic image may be performed, and the position of the photoacoustic wave generating source may be detected from the photoacoustic image after noise reduction. FIG. 12 shows a part of the configuration of a photoacoustic image generation apparatus in the case of detecting the position of a photoacoustic wave generating source from a photoacoustic image after noise reduction. In this case, the ultrasound unit 12 (refer to FIG. 1) has a noise reduction processing unit 34 between the photoacoustic image generation unit 25 and the sound source position detection unit 30.

A photoacoustic image generated by the photoacoustic image generation unit 25 is input to the noise reduction processing unit 34. The noise reduction processing unit 34 performs noise reduction filtering processing for reducing noise from a photoacoustic image. Examples of the noise reduction filtering processing include Gaussian filtering processing or median filtering processing for adding up pixels in a predetermined region. For example, in the median filtering processing or the Gaussian filtering processing, the addition is performed within the range of four pixels in radius from the observed pixel. By performing the median filtering processing or the Gaussian filtering processing, it is possible to reduce noise present in the image.

It is conceivable that a photoacoustic wave generated in the light absorption member 157 (refer to FIG. 3) of the insertion needle 15 changes depending on the size and type of the insertion needle 15. When performing median filtering processing or Gaussian filtering processing, the noise reduction processing unit 34 may perform the filtering processing by adding pixels in a region, which matches the magnitude of the photoacoustic wave generated from the insertion needle 15, according to the insertion needle 15 to be used. For example, the correspondence relationship between the type of the insertion needle 15 and the size of a region to add up the pixel values in the median filtering processing or the Gaussian filtering processing may be stored, and the size of a region to add up the pixel values may be selected according to the insertion needle 15 to be used. The sound source position detection unit 30 receives a photoacoustic image after performing the noise reduction filtering processing from the noise reduction processing unit 34, and detects the position of the photoacoustic wave generating source from the photoacoustic image. By reducing noise, it is possible to reduce a possibility of detecting an incorrect position as the position of the photoacoustic wave generating source.

Instead of or in addition to the median filtering processing or the Gaussian filtering processing, the noise reduction processing unit 34 may perform filtering processing for reducing electrical noise, which is commonly incorporated to positions in the same depth direction, in the detection signals detected by a plurality of detector elements of the probe 11. Specifically, processing for adding the detection signals of a plurality of detector elements to be simultaneously detected or performing averaging after adding the detection signals at each depth position and subtracting a signal obtained by the addition or a signal obtained by the averaging from the detection signal detected by each detector element may be performed.

Figure 13:
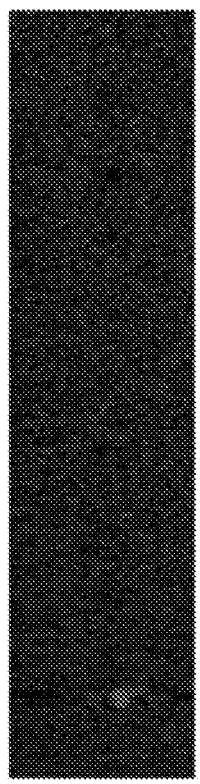
FIG. 13 is a diagram showing a photoacoustic image subjected to filtering processing for reducing electrical noise that is commonly incorporated to positions in the same depth direction.

FIG. 13 shows a photoacoustic image subjected to filtering processing for reducing electrical noise that is commonly incorporated to positions in the same depth direction. Referring to FIG. 8, particularly in the region A 62 (refer to FIG. 6), electrical noise is commonly incorporated to positions in the same depth direction, and horizontal streaks appear in the image. The image shown in FIG. 13 is obtained by performing filtering processing for reducing electrical noise, which is commonly incorporated to positions in the same depth direction, for a part of the region A 62. Referring to FIG. 13, it can be seen that horizontal streaks have been removed. By detecting the position of the photoacoustic wave generating source from such an image, it is possible to improve the detection accuracy of the position of the photoacoustic wave generating source.

Although the noise reduction processing is performed as pre-processing of the processing for detecting the photoacoustic wave generating source in the above explanation, the present invention is not limited thereto, and a photoacoustic image after noise reduction filtering processing may be used in processing other than the processing for detecting the photoacoustic wave generating source. For example, the first signal acquisition unit 31 may acquire the S value from a photoacoustic image after performing filtering processing for reducing electrical noise that is commonly incorporated to positions in the same depth direction. In addition, the second signal acquisition unit 32 may acquire the N value from a photoacoustic image after performing filtering processing for reducing electrical noise that is commonly incorporated to positions in the same depth direction.

In addition, although the example in which the light guide member 155 is embedded into the tube 158 using the transparent resin 159 and the light absorption member 157 is disposed at the distal end of the transparent resin 159 has been described in FIG. 3, the present invention is not limited thereto. For example, a film having a light absorption property may be used as the light absorption member 157 to cover the light emitting portion 156, which is the light emitting surface of the light guide member 155, with the film having a light absorption property, and the light guide member 155 may be embedded into the transparent resin. Alternatively, a gap may be provided between the light emitting portion 156 of the light guide member 155 and the light absorption member 157, so that the light emitting portion 156 and the light absorption member 157 face each other with the air layer interposed therebetween.

In addition, although the example in which the inner needle 152 has the tube 158 has been described in FIG. 3, the present invention is not limited thereto. For example, an inner needle may be formed of a material having a light absorption property, for example, black resin, and the light guide member 155 may be embedded thereinside. In this case, the inner needle, in particular, the distal end portion of the inner needle also serves as the light absorption member 157 that absorbs light, which is emitted from the light emitting portion 156 of the light guide member 155, to generate an acoustic wave. Instead of embedding the light guide member 155 into the resin, the light guide member 155 having almost the same outer diameter as the inner diameter of the insertion needle body 151 may be used, and the light guide member 155 itself may be used as an inner needle. In this case, a film having a light absorption property, for example, a black fluorine resin may be used as the light absorption member 157, so that at least a part of the light guide member 155 including the light emitting portion 156 is covered by the black fluorine resin.

Although the example in which the insertion needle 15 has the insertion needle body 151, which forms an outer needle, and the inner needle 152 has been described in the above embodiment, the inner needle 152 is not essential. In a case where the insertion needle 15 does not have an inner needle, the light guide member 155 may be inserted into the inner cavity of the insertion needle body 151, and the light absorption member 157 may be provided at a position, to which light emitted from the light emitting portion 156 is emitted, on the inner wall of the insertion needle body 151. The light absorption member 157 may also serve as a fixing member for fixing the distal end portion of the light guide member 155 to the inner cavity of the insertion needle body 151. The light guide member 155, such as an optical fiber, may be fixed to the inner wall by an adhesive within the inner cavity of an insert, such as an insertion needle. Alternatively, a hollow tube having a smaller diameter than the inner cavity may be provided in the inner cavity of an insert, and the light guide member 155 may be fixed by the tube.

The light absorption member 157 is not essential. For example, the light emitted from the light emitting portion 156 may be emitted to the insertion needle body 151, and a portion of the insertion needle body 151 to which light is emitted may become a photoacoustic wave generating portion and a photoacoustic wave may be generated from the portion. For example, a light emitting portion and a photoacoustic wave generating portion may be disposed in the vicinity of the distal end of the insertion needle 15, so that the photoacoustic wave is generated in the vicinity of the distal end of the insertion needle 15. The "vicinity" of the distal end of the insertion needle 15 referred to herein means a position where it is possible to generate photoacoustic waves capable of imaging the position of the distal end of the insertion needle 15 with accuracy, which is required for insertion work, in a case where the light emitting portion and the photoacoustic wave generating portion are disposed at the position. For example, "vicinity" indicates the range of 0 mm to 3 mm toward the proximal end side from the distal end of the insertion needle 15.

The insertion needle 15 is not limited to being percutaneously inserted into the subject from the outside of the subject, and a needle for ultrasound endoscope may be used. The light guide member 155 and the light absorption member 157 may be provided in the needle for ultrasound endoscope, light may be emitted to the light absorption member 157 provided in the distal end portion of the needle, and photoacoustic waves may be detected to generate a photoacoustic image. In this case, it is possible to insert the needle for ultrasound endoscope while checking the position of the distal end portion of the needle for ultrasound endoscope by observing the photoacoustic image. The photoacoustic wave generated in the distal end portion of the needle for ultrasound endoscope may be detected using a probe for body surface, or may be detected using a probe built into the endoscope.

In the embodiment described above, the insertion needle 15 has been considered as an insert. However, the insertion needle 15 is not limited thereto. The insert may be a needle for radiofrequency ablation in which an electrode used in radiofrequency ablation is housed, or may be a catheter inserted into the blood vessel, or may be a guide wire of the catheter inserted into the blood vessel. Alternatively, the insert may be an optical fiber for laser treatment.

Although the needle having an opening at the distal end is assumed as a needle in the embodiment described above, the opening does not necessarily need to be provided in the distal end portion. The needle is not limited to a needle, such as an injection needle, and may be a biopsy needle used for a biopsy. That is, a biopsy needle that can be inserted into the examination target of the body in order to sample the tissue in the examination target may be used. In this case, photoacoustic waves may be generated in a sampling portion (inlet port) for sampling the tissue of a biopsy part by sucking the tissue. In addition, a needle may be used as a guiding needle for insertion up to a deep portion, such as a subcutaneous part or intra-abdominal organs.

In FIG. 1, only one insertion needle 15 is drawn. However, the number of inserts to be imaged in a photoacoustic image is not limited to one. A plurality of sets of inserts and laser units corresponding thereto may be prepared, and a photoacoustic image may be generated for each insert so that the position of each insert can be checked through the photoacoustic image. In this case, the S value and the N value may be acquired for each insert, and the number of light emissions and the light emission interval may be controlled for each insert based on the ratio between the S value and the N value. During image display, the color of a photoacoustic image may be changed for each insert, and the photoacoustic image with the changed color may be made to overlap the ultrasound image. In this case, it is possible to distinguish between a plurality of inserts in the image.

Figure 14:
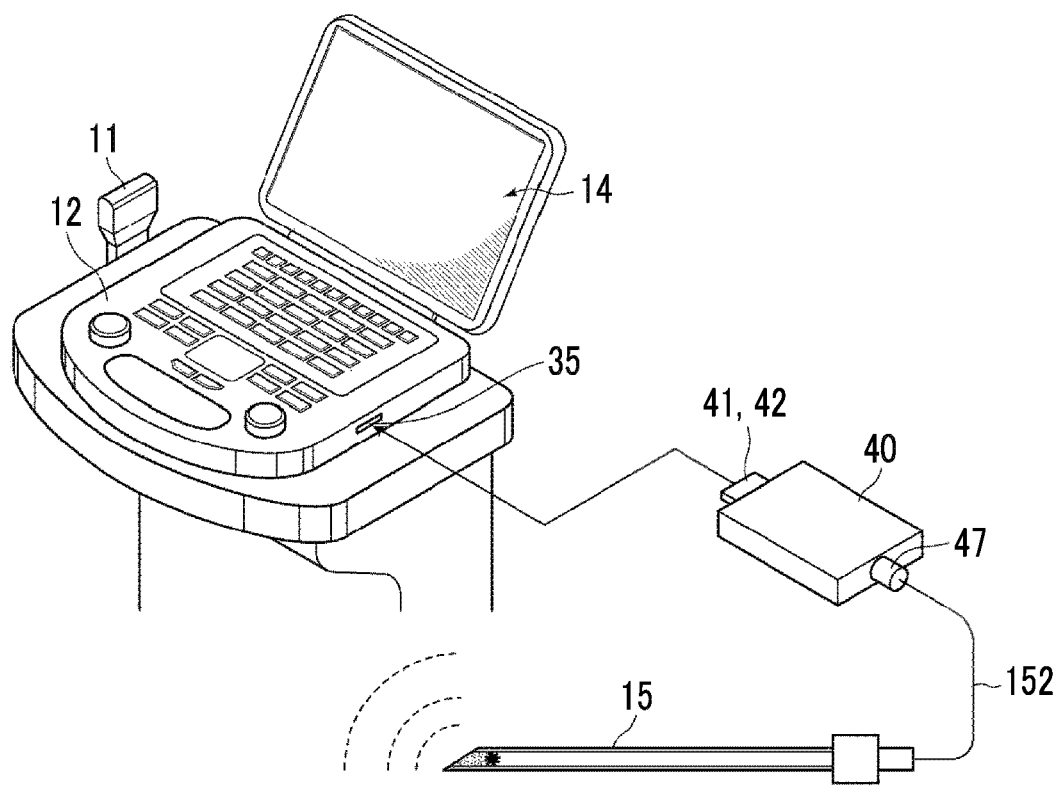
FIG. 14 is a diagram showing the appearance of a photoacoustic image generation apparatus.

Finally, FIG. 14 shows the appearance of a photoacoustic image generation apparatus. The probe 11 is connected to the ultrasound unit 12. The ultrasound unit 12 is configured as an integrated device including the image display unit 14. The ultrasound unit 12 typically has a processor, a memory, a bus, and the like. A program regarding photoacoustic image generation is installed in the ultrasound unit 12. The ultrasound unit 12 has a USB port 35. A USB connector including a power input terminal 41 and a trigger input terminal 42 of a laser unit 13 is inserted into the USB port 35. In a case where the laser unit 13 is a card-sized small and lightweight device, it is possible to hold the USB connector by inserting the USB connector into the USB port of the ultrasound unit 12.

One end of the optical fiber 16 is connected to an optical output terminal 47 of the laser unit 13, and the other end is connected to a proximal end portion of the insertion needle 15. The optical fiber 16 is inserted into the optical output terminal 47, and is held by spring force, for example. If the operator applies a strong force to the optical output terminal 47, for example, by pulling the insertion needle 15, the optical fiber exits from the optical output terminal 47. Accordingly, it is possible to prevent the optical fiber from being broken. The optical fiber 16 can also be used as the light guide member 155 (refer to FIG. 3) inside the insertion needle. In this case, by making it possible to directly insert or remove the optical fiber 16 into or from the optical output terminal 47, there is an effect that the cost can be reduced without providing a connector in the optical fiber 16 extending from the insertion needle 15.

Pulse energy of the pulsed laser light output from the laser unit 13 can be set to 6.4 if the core diameter of the optical fiber forming the light guide member 155 is 200 μm. The pulse energy of the pulsed laser light can be set to 2.0 μJ if the core diameter of the optical fiber is 100 μm. The pulse time width can be set to 80 ns. The pulse repetition rate can be realized up to 3300 Hz at the highest, for example.

In FIG. 14, the optical output terminal 47 is provided on a surface opposite to a surface on which the USB connector including the power input terminal 41 and the trigger input terminal 42 is present. However, it is preferable that the optical output terminal 47 is provided on a surface perpendicular to the surface on which the USB connector is present. In a case where the USB connector and the optical output terminal 47 are provided on the opposite surfaces, if the laser unit 13 is pulled when the operator moves the insertion needle 15, the USB connector may exit from the USB port 35. In contrast, in a case where the USB connector and the optical output terminal 47 are provided on the surfaces perpendicular to each other, the USB connector is difficult to exit from the USB port 35 even if the laser unit 13 is pulled.

In FIG. 14, the laser unit 13 is directly connected to the USB port 35. However, the present invention is not limited thereto, and the USB port 35 and the laser unit 13 may be connected to each other using an extension cable or the like. The trigger input terminal 42 does not need to be included in the USB connector, and the laser unit 13 may acquire a trigger signal from a connector (terminal) different from the USB port 35. For example, a trigger signal may be acquired from a connector for electrocardiogram (ECG) measurement attached to the normal ultrasound system. Alternatively, a trigger signal may be acquired from some terminals of the connector of the probe.

While the present invention has been described based on the preferred embodiment, the photoacoustic image generation apparatus, the signal processing device, and the photoacoustic image generation method of the present invention are not limited to the above embodiment, and various modifications and changes in the configuration of the above embodiment are also included in the range of the present invention.

EXPLANATION OF REFERENCES

10: photoacoustic image generation apparatus
11: probe
12: ultrasound unit
13: laser unit
14: image display unit
15: insertion needle
16: optical fiber
21: receiving circuit
22: AD conversion unit
24: data separation unit
25: photoacoustic image generation unit
26: ultrasound image generation unit
27: image combining unit
28: control unit
29: transmission control circuit
30: sound source position detection unit
31: first signal acquisition unit
32: second signal acquisition unit
33: light emission control unit
34: noise reduction processing unit
35: USB port
41: power input terminal
42: trigger input terminal
47: optical output terminal
51: averaging unit
52: photoacoustic image reconstruction unit
53: detection and logarithmic conversion unit
54: photoacoustic image construction unit
55: noise reduction processing unit
61: sound source position
62, 63: region
64 to 66: region
151: insertion needle body (outer needle)
152: inner needle
153: inner needle base
154: outer needle base
155: light guide member
156: light emitting portion
157: light absorption member
158: tube
159: transparent resin

What is claimed is:

1. A photoacoustic image generation apparatus, comprising: a laser unit;
an insertion needle at least a part of which is configured to be insertable into a subject and which has an optical fiber for guiding light emitted from the laser unit, a light emitting end surface of the optical fiber that emits light guided by the optical fiber, and a light absorption member that generates at least one photoacoustic wave of a plurality of photoacoustic waves due to absorption of the light emitted from the light emitting end surface of the optical fiber, wherein the light emitted includes a number of a plurality of light emissions, and wherein the at least one photoacoustic wave generated corresponds to at least one light emission of the plurality of light emissions;
a probe that detects a photoacoustic wave emitted from the insertion needle after at least a part of the insertion needle is inserted into the subject; and
a processor,
the processor configured to:
generate a photoacoustic image based on a plurality of detection signals of the at least one photoacoustic wave;
detect a position of a generation source of the at least one photoacoustic wave from the photoacoustic image;
acquire a first signal value indicating an intensity of the at least one photoacoustic wave emitted from the generation source of the at least one photoacoustic wave;
acquire a second signal value, which indicates noise in the photoacoustic image, wherein the second signal value is acquired in a region away from the generation source of the at least one photoacoustic wave by a predetermined distance;
obtain a difference signal value of the generated photoacoustic image by dividing the first signal value by the second signal value, wherein the difference signal value is representative of a signal to noise (SN) ratio between the first signal value and the second signal value;
compare the SN ratio to a predetermined target range for the difference signal value, wherein the predetermined target range including a first threshold value and a second threshold value, wherein the first and second threshold values represent a lower limit and an upper limit of the predetermined target range, respectfully, and wherein the second threshold value is larger than the first threshold value;
control the number of light emissions of the plurality of light emissions and a light emission interval of the laser unit for one the generation of the photoacoustic image, such that:
when the obtained difference signal value is smaller than the first threshold value, make the number of light emissions of the plurality of light emissions larger than a current number of light emissions of the laser unit and make the light emission interval shorter than a current light emission interval of the laser unit, or
when the obtained difference signal value is larger than the second threshold value, make the number of light emissions of the plurality of light emissions smaller than the current number of light emissions of the laser unit and make the light emission interval longer than the current light emission interval of the laser unit; and
wherein the number of light emissions and the light emission interval of the laser unit are controlled so that the difference signal value falls within the predetermined target range to improve image quality of the generated photoacoustic image; and
generate the photoacoustic image by at least adding a number of the plurality of detection signals of the plurality of photoacoustic waves corresponding to the number of light emissions.

2. The photoacoustic image generation apparatus according to claim 1,
wherein the processor is further configured to make the laser unit emit light at equal intervals until generation of a next photoacoustic image after generation of one photoacoustic image.

3. The photoacoustic image generation apparatus according to claim 1, wherein the processor is further configured to detect a position of a pixel having a maximum pixel value in the photoacoustic image as the position of the generation source of the photoacoustic wave.

4. The photoacoustic image generation apparatus according to claim 1, wherein the processor is further configured to acquire, as the first signal value, a pixel value of a pixel of a photoacoustic image at the position of the generation source of the photoacoustic wave or a signal value of a detection signal of the photoacoustic wave.

5. The photoacoustic image generation apparatus according to claim 1, wherein the processor is further configured to acquire, as the first signal value, a value obtained by subtracting an average value of pixel values of the photoacoustic image corresponding to a plurality of positions around the position of the generation source of the photoacoustic wave from a pixel value of a pixel of a photoacoustic image at the position of the generation source of the photoacoustic wave, or a value obtained by subtracting an average value of signal values of detection signals of the photoacoustic waves corresponding to a plurality of positions around the position of the generation source of the photoacoustic wave from a signal value of a detection signal of the photoacoustic wave at the position of the generation source of the photoacoustic wave.

6. The photoacoustic image generation apparatus according to claim 1, wherein the processor is further configured to calculate a variance of pixel values of the photoacoustic image corresponding to a plurality of positions around the position of the generation source of the photoacoustic wave and acquire the calculated variance of pixel values as the second signal value, or calculate a variance of signal values of detection signals of the photoacoustic waves corresponding to the plurality of positions around the position of the generation source of the photoacoustic wave and acquire the calculated variance of signal values as the second signal value.

7. The photoacoustic image generation apparatus according to claim 1, wherein the probe further detects a reflected acoustic wave of an acoustic wave transmitted toward the subject, and the processor is further configured to generate a reflected acoustic wave image based on the reflected acoustic wave is further provided.

8. The photoacoustic image generation apparatus according to claim 7, wherein the processor is further configured to generate the photoacoustic image and the reflected acoustic wave image, respectively, and the number of photoacoustic images generated per unit time and the number of reflected acoustic wave images generated per unit time are the same.

9. The photoacoustic image generation apparatus according to claim 7, wherein the probe includes at least a plurality of detector elements arranged in a one-dimensional manner, and detects the reflected acoustic wave by performing a scan while shifting an acoustic line by one line at a time.

10. The photoacoustic image generation apparatus according to claim 9, wherein the processor is further configured to make the laser unit emit light between scans of the acoustic lines.

11. The photoacoustic image generation apparatus according to claim 10, wherein the processor is further configured to control emission of the laser unit with reference to a look-up table in which the number of light emissions is associated with an emission timing for determining between which scanning positions in detection of a reflected ultrasound wave each emission is to be performed.

12. The photoacoustic image generation apparatus according to claim 6, wherein the processor is further configured to combine the photoacoustic image and the reflected acoustic wave image.

13. The photoacoustic image generation apparatus according to claim 1, wherein the processor is further configured to perform noise reduction filtering processing for reducing noise of the photoacoustic image, and detect the position of the generation source of the photoacoustic wave from a photoacoustic image after performing the noise reduction filtering processing.

14. The photoacoustic image generation apparatus according to claim 13, wherein the noise reduction filtering processing is median filtering processing or Gaussian filtering processing.

15. The photoacoustic image generation apparatus according to claim 13, wherein the noise reduction filtering processing is filtering processing for reducing noise incorporated to positions in the same depth direction in detection signals of a plurality of elements.

16. The photoacoustic image generation apparatus according to claim 1, further comprising:

an image display unit that displays the photoacoustic image, a maximum value of the first signal value, and a current first signal value on a screen.

17. A signal processing device, comprising:

a receiving circuit that receives a detection signal of a photoacoustic wave emitted from an insertion needle at least a part of which is inserted into a subject and which has an optical fiber for guiding light emitted from a laser unit, a light emitting end surface of the optical fiber that emits light guided by the optical fiber, and a light absorption member that generates at least one a photoacoustic wave of a plurality of photoacoustic waves due to absorption of the light emitted from the light emitting end surface of the optical fiber, wherein the light emitted includes a number of a plurality of light emissions, and wherein the at least one photoacoustic wave generated corresponds to at least one light emission of the plurality of light emissions; and a processor, wherein the processor is configured to:
generate a photoacoustic image based on a plurality of detection signals of the photoacoustic wave;
detect a position of a generation source of the at least one photoacoustic wave from the photoacoustic image;
acquire a first signal value indicating an intensity of the at least one photoacoustic wave emitted from the generation source of the at least one photoacoustic wave;
acquire a second signal value, which indicates noise in the photoacoustic image, wherein the second signal value is acquired in a region away from the generation source of the at least one photoacoustic wave by a predetermined distance;

obtain a difference signal value by dividing the first signal value by the second signal value, wherein the difference signal value is representative of a signal to noise (SN) relative magnitude relationship between the first signal value and the second signal value;

compare the SN relative magnitude relationship to a predetermined target range for the difference signal value, wherein the predetermined target range including a first threshold value and a second threshold value, wherein the first and second threshold values represent a lower limit and an upper limit of the predetermined target range, respectfully, and wherein the second threshold value is larger than the first threshold value;

control the number of light emissions of the plurality of light emissions and a light emission interval of the laser unit for the generation of the photoacoustic image, such that:

when the obtained difference signal value is smaller than the first threshold value, make the number of light emissions of the plurality of light emissions larger than a current number of light emissions of the laser unit and make the light emission interval shorter than a current light emission interval of the laser unit, and when the obtained difference signal value is larger than the second threshold value, make the number of light emissions of the plurality of light emissions smaller than the current number of light emissions of the laser unit and make the light emission interval longer than the current light emission interval of the laser unit;

wherein the number of light emissions and the light emission interval of the laser unit are controlled so that the difference signal value falls within the predetermined target range to improve image quality of the generated photoacoustic image; and generate the photoacoustic image by at least adding a number of the plurality of detection signals of the plurality of photoacoustic waves corresponding to the number of light emissions.

18. A photoacoustic image generation method, comprising:

receiving a detection signal of a photoacoustic wave emitted from an insertion needle having an optical fiber for guiding light emitted from a laser unit, a light emitting end surface of the optical fiber that emits light guided by the optical fiber, and a light absorption member that generates a at least one photoacoustic wave of a plurality of photoacoustic waves due to absorption of the light emitted from the light emitting end surface of the optical fiber, wherein the light emitted includes a number of a plurality of light emissions, and wherein the at least one photoacoustic wave generated corresponds to at least one light emission of the plurality of light emissions;

generating a photoacoustic image based on a plurality of detection signals of the at least one photoacoustic wave;

detecting a position of a generation source of the at least one photoacoustic wave from the photoacoustic image;

acquiring a first signal value indicating an intensity of the at least one photoacoustic wave emitted from the generation source of the at least one photoacoustic wave;

acquiring a second signal value, which indicates noise in the photoacoustic image, wherein the second signal value is acquired in a region away from the generation source of the at least one photoacoustic wave by a predetermined distance;

obtaining a difference signal value by dividing the first signal value by the second signal value, wherein the difference signal value is representative of a signal to noise (SN) relative magnitude relationship between the first signal value and the second signal value;

comparing the SN relative magnitude relationship to a predetermined target range for the difference signal value, wherein the predetermined target range including a first threshold value and a second threshold value, wherein the first and second threshold values represent a lower limit and an upper limit of the predetermined target range, respectfully, and wherein the second threshold value is larger than the first threshold value; and providing a processor, the processor configured to control the number of light emissions of the plurality of light emissions and a light emission interval of the laser unit for the generation of the photoacoustic image, such that:

when the obtained difference signal value is smaller than the first threshold value, make the number of light emissions of the plurality of light emissions larger than a current number of light emissions of the laser unit and make the light emission interval shorter than a current light emission interval of the laser unit, and when the obtained difference signal value is larger than the second threshold value, make the number of light emissions of the plurality of light emissions smaller than the current number of light emissions of the laser unit and make the light emission interval longer than the current light emission interval of the laser unit;

wherein the number of light emissions and the light emission interval of the laser unit are controlled so that the difference signal value falls within the predetermined target range to improve image quality of the generated photoacoustic image; and wherein, in generating the photoacoustic image, the photoacoustic image is generated by at least adding a number of the plurality of detection signals of the plurality of photoacoustic waves corresponding to the number of light emissions.

* * * * *